(12) United States Patent
Javanmard et al.

(10) Patent No.: US 11,506,592 B2
(45) Date of Patent: Nov. 22, 2022

(54) WEARABLE IMPEDANCE CYTOMETER

(71) Applicant: Rutgers, the State University of New Jersey, New Brunswick, NJ (US)

(72) Inventors: Mehdi Javanmard, West Windsor, NJ (US); Abbas Furniturewalla, Collegeville, FL (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 526 days.

(21) Appl. No.: 16/656,148

(22) Filed: Oct. 17, 2019

(65) Prior Publication Data

US 2020/0124519 A1 Apr. 23, 2020

Related U.S. Application Data

(60) Provisional application No. 62/748,362, filed on Oct. 19, 2018.

(51) Int. Cl.
| | |
|---|---|
| *G01N 15/14* | (2006.01) |
| *G01N 15/02* | (2006.01) |
| *G01N 15/12* | (2006.01) |
| *G01N 33/483* | (2006.01) |
| *G01N 15/00* | (2006.01) |
| *G01N 15/10* | (2006.01) |

(52) U.S. Cl.
CPC ......... *G01N 15/1404* (2013.01); *G01N 15/02* (2013.01); *G01N 15/1209* (2013.01); *G01N 33/4836* (2013.01); *G01N 2015/008* (2013.01); *G01N 2015/0073* (2013.01); *G01N 2015/1006* (2013.01)

(58) Field of Classification Search
None
See application file for complete search history.

(56) References Cited

U.S. PATENT DOCUMENTS

| | | | |
|---|---|---|---|
| 2010/0141938 A1* | 6/2010 | Banerjee | G01N 21/31 356/246 |
| 2014/0190830 A1 | 7/2014 | Sturmer et al. | |
| 2015/0212039 A1* | 7/2015 | Lieber | H04N 1/00196 422/69 |

FOREIGN PATENT DOCUMENTS

WO 2019/236682 A1 12/2019

* cited by examiner

*Primary Examiner* — Ann Montgomery
(74) *Attorney, Agent, or Firm* — Fox Rothschild LLP

(57) ABSTRACT

This disclosure provides an impedance cytometer which includes a carrier that can be attached to a living being, with a biosensor mounted thereto. The bio sensor includes a microfluidic flow channel, formed in the carrier, and an impedance circuit. The microfluidic flow channel accommodates passage of a particle therethrough. The impedance circuit, connected to the microfluidic flow channel, includes a signal generator that produces a high-frequency drive signal applied to the flow channel to produce a biosensor output signal having high-frequency variation resulting from the drive signal and low-frequency variation resulting from impedance variation within the flow channel during the particle's passage. A lock-in amplifier is disposed to (i) amplify the bio sensor output signal, (ii) mix the amplified signal with the drive signal, and (iii) frequency-filter the mixed, amplified signal to output an impedance signal representing the low-frequency impedance variation resulting from the passage of the particle. Embodiments enable wearable, personalized cytometry.

37 Claims, 15 Drawing Sheets

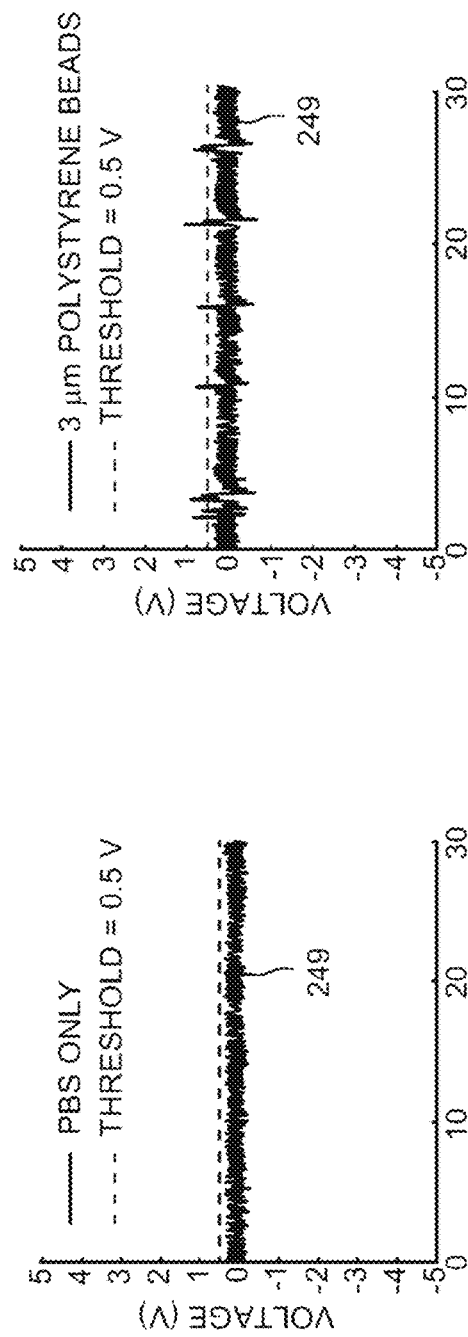
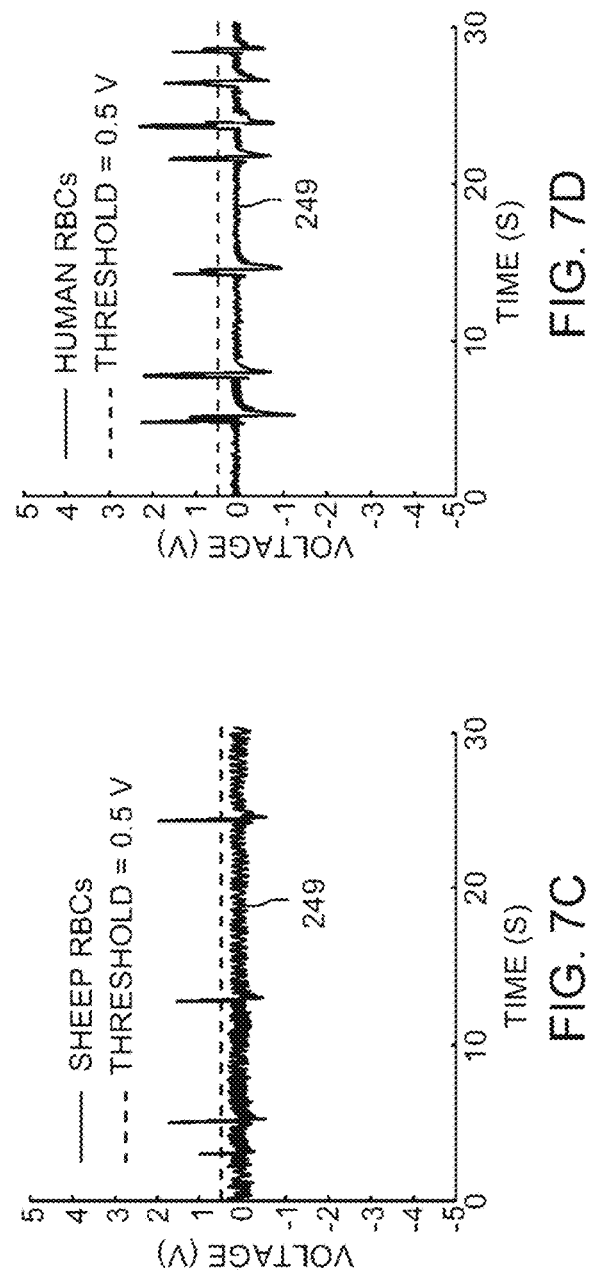
FIG. 7A
FIG. 7B
FIG. 7C
FIG. 7D

WEARABLE IMPEDANCE CYTOMETER

CROSS-REFERENCE TO RELATED APPLICATIONS

This application claims priority under 35 U.S.C. § 119(e) to U.S. Provisional Patent Application No. 62/748,362, filed Oct. 19, 2018. The foregoing application is incorporated by reference herein in its entirety.

STATEMENT REGARDING FEDERALLY SPONSORED RESEARCH

This invention was made with government support under Grant Numbers 1556253 from National Science Foundation and NNX16AO69A from the Baylor College of Medicine Translational Research Institute for Space Health through NASA. The government has certain rights in the invention.

FIELD OF THE INVENTION

This disclosure relates to an impedance cytometer, which includes a carrier that can be attached to a living being, with a bio sensor mounted thereto.

BACKGROUND OF THE INVENTION

Generally, flow cytometry is a specialized technology whereby cells, biomarkers, and particles are quantified. Cell counting is an application of flow cytometry and can provide significant insight into a patient's health. A well-known example includes a complete blood count (CBC) test, which can yield information about low or high red blood cell (RBC), white blood cell (WBC), or platelet levels amongst many other specific biomarker counts.

Common approaches for counting cells most commonly employ fluorescence or impedance-based measurements. Fluorescence-based cytometers require the labeling of biological cells with antibodies functionalized with fluorophores. Continuous cell counting has been demonstrated in vivo using fluorescence-based flow cytometers. Impedance cytometry, which utilizes electrical measurements, is an alternative technique that does not require the labeling procedure. Impedance cytometry can be used to detect cells, proteins, and nucleic acids.

Existing optical instrumentation required to analyze fluorescent particles is typically bulky and expensive, and the related labeling procedure that is required is tedious. Impedance cytometry does not require the labeling procedure and can be used to detect cells, proteins, and nucleic acids. The market offers powerful and versatile coulter counters, such as CytoFLEX™ (Beckman Coulter, Inc., Brea, Calif., USA). However, these benchtop instruments are relatively large in size and have yet to be made portable or wearable.

Modern coulter counting has been demonstrated using inexpensive circuitry with miniaturized footprints optimized for application-specific tasks, such as blood cell counting. However, these cytometry systems are not designed to be handled by a patient, as they rely on expensive external data acquisition hardware and are not packaged into a convenient, user-friendly product. Furthermore, existing prototypes of portable cytometry systems have been implemented on rigid circuit boards that cannot be worn or implanted and do not allow continuous and automated counting of blood cells or other particles.

Moving away from expensive data acquisition hardware has been a challenge because microfluidic impedance cytometry requires reading highly sensitive signals on the scale of nanovolts, which fall below the noise level of the environment. Furthermore, the signal's baseline may drift over an extended period, reducing the amount of post-gain amplification that can be applied to the signal and demanding the use of powerful data acquisition instrumentation with high-resolution (>16 bit) analog-to-digital converters (ADCs). Because of the small, sensitive signals, existing impedance cytometers typically use Faraday cages, which are often heavy and large, for isolation from electromagnetic waves.

Accordingly, there remains a pressing need for a new and improved impedance cytometers.

SUMMARY OF THE INVENTION

Various embodiments described in this document address the above-mentioned unmet needs and/or other needs by providing novel impedance cytometers and uses thereof.

In one aspect, this disclosure provides an impedance cytometer, e.g., a wearable impedance cytometer. The impedance cytometer includes (i) a carrier configured to be attached to a living being; and (ii) a biosensor mounted to the carrier. The biosensor comprises: a microfluidic flow channel formed therein, wherein the microfluidic flow channel is structured to accommodate passage of a particle therethrough; and an impedance circuit, connected to the microfluidic flow channel, wherein the impedance circuit includes a signal generator that produces a high-frequency drive signal that is applied to the microfluidic flow channel to produce thereby a bio sensor output signal, and wherein the impedance circuit delivers a bio sensor output signal having a high-frequency variation resulting from application of the high-frequency drive signal to the microfluidic flow channel, the bio sensor output signal further having a low-frequency variation resulting from an impedance variation within the microfluidic flow channel during the passage of the particle therethrough; and (iii) a lock-in amplifier disposed to receive the biosensor output signal, wherein the lock-in amplifier: amplifies the biosensor output signal, mixes the amplified biosensor output signal with the high-frequency drive signal, and frequency-filters the mixed, amplified biosensor output signal to output an impedance signal representing the low-frequency impedance variation resulting from the passage of the particle through the microfluidic channel.

In another aspect, this disclosure further provides a method for identifying or counting particles in a sample from a subject. The method comprises (a) obtaining from a subject a sample comprising particles, through a carrier configured to be attached to a subject; (b) analyzing the sample by the impedance cytometer as described above; and (c) determining a type or a count of the particles based on the outputted impedance signal representing the low-frequency impedance variation resulting from the passage of the particle through the microfluidic channel.

In some embodiments, the carrier may be configured to be removably attached to the living being via a leg band, an armband, a waistband, such as a belt, or a wristband. The carrier may be further configured to be attached to the living being via a necklace. The carrier may be a flexible printed circuit board (PCB) or a rigid PCB. The carrier may be a complementary metal-oxide-semiconductor (CMOS) chip.

In some embodiments, the microfluidic flow channel can be removably mounted in the biosensor. In some embodiments, the microfluidic flow channel may include a main channel and a side channel. The side channel can be attached to the main channel to divert a portion of the passage of the particle in the main channel. The main channel may have a larger width than the side channel. In some embodiments, the main and side channels are orthogonal relative to each other. In some embodiments, the concentration of the particles in the side channel is about 2000 folds or less than the concentration of the particles in the main channel, thereby the particles in the side channel can be subject to analysis without dilution.

In some embodiments, the microfluidic flow channel may be configured to receive the particle via a catheter, a needle, or an array of needles connected to the living being. In some embodiments, the microfluidic flow channel may be formed of polydimethylsiloxane (PDMS).

In some embodiments, the particle can be a cell, a bacterium, a virus, a protein, a microparticle, a nanoparticle, a nucleic acid, a biomarker, or a bead with a biological material attached thereto. In some embodiments, the particle can be any microbial cellular organism.

In some embodiments, the microfluidic flow channel is configured to receive the particle suspended in a bodily fluid (e.g., blood) or a buffer solution. In some embodiments, the microfluidic flow channel is configured to receive the particle selected from the group consisting of red blood cell, white blood cell, platelet, hematocrit, hemoglobin, neutrophil, lymphocyte, microbial, and a combination thereof.

The signal generator may be further configured to produce the high-frequency drive signal with a plurality of high frequencies. The lock-in amplifier may be further configured to frequency-filter the mixed, amplified bio sensor output signal with a low-pass filter cutoff frequency larger than an inverse of a transit time of the particle to traverse an electric field created by the high-frequency drive signal in the microfluidic flow channel. The lock-in amplifier may include an amplifier, a mixer, and a frequency filter.

The impedance cytometer may further include a DC blocker configured to remove a DC baseline from the impedance signal, an amplifier configured to amplify the impedance signal, or an analog-to-digital converter (ADC) configured to output a digitized form of the impedance signal. The ADC may have 10 bits or fewer or 8 bits or fewer. The impedance cytometer may further include a wired or wireless transmission module configured to transmit the digitized form of the impedance signal.

An impedance cytometer system may include any impedance cytometer described above, together with a microprocessor configured to receive and analyze the digitized form of the impedance signal. The system may further include a display configured to show a result of the analysis of the impedance signal. The microprocessor, the display, or both may form part of the impedance cytometer and may be mounted to the carrier. Alternatively, the microprocessor, the display, or both may form part of the broader impedance cytometer and may receive data that originate at, and are transmitted by, the impedance cytometer to a different device, such as a smartphone, of with the microprocessor or display forms a part. The result of the analysis may include a particle count, an identification of the particle, a characterization of the particle, or an indication of a health condition of the living being.

The impedance cytometer may further include a microprocessor mounted to the carrier, the microprocessor configured to receive and analyze a digitized form of the impedance signal. The impedance cytometer may further include a display mounted to the carrier and configured to show a result of the analysis of the impedance signal.

The foregoing summary is not intended to define every aspect of the disclosure, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the disclosure, are given by way of illustration only, because various changes and modifications within the spirit and scope of the disclosure will become apparent to those skilled in the art from this detailed description.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIGS. 7A, 7B, 7C, 7D, and 7E are a set of graphs of data exported from a smartphone application having the interface shown in FIGS. 5A-5B, tested using no particles, 3-micron polystyrene bead particles, sheep red blood cell particles, and human red blood cell particles, respectively. FIG. 7E shows the same data illustrated in FIG. 7C, as seen on a smartphone application graphical user interface.

DETAILED DESCRIPTION OF THE INVENTION

Figure 1A:
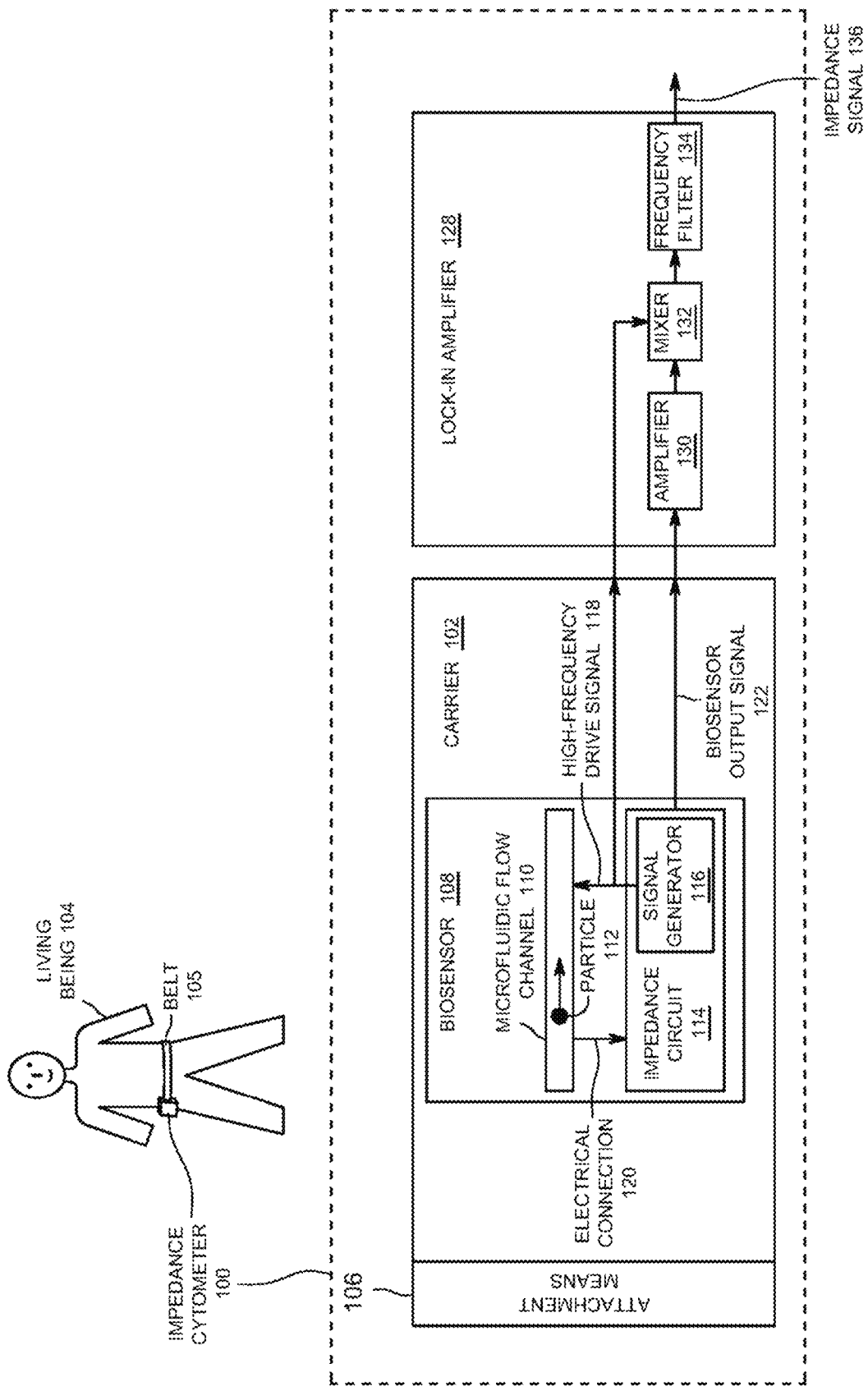
FIG. 1A is a block diagram illustrating a general embodiment impedance cytometer configured to be attached to a living being.

This disclosure in one aspect provides an impedance cytometer, e.g., a wearable impedance cytometer. The impedance cytometer includes (i) a carrier configured to be attached to a living being; and (ii) a biosensor mounted to the carrier. The biosensor comprises: a microfluidic flow channel formed therein, wherein the microfluidic flow channel is structured to accommodate passage of a particle therethrough; and an impedance circuit, connected to the microfluidic flow channel, wherein the impedance circuit includes a signal generator that produces a high-frequency drive signal that is applied to the microfluidic flow channel to produce thereby a bio sensor output signal, and wherein the impedance circuit delivers a bio sensor output signal having a high-frequency variation resulting from application of the high-frequency drive signal to the microfluidic flow channel, the bio sensor output signal further having a low-frequency variation resulting from an impedance variation within the microfluidic flow channel during the passage of the particle therethrough; and (iii) a lock-in amplifier disposed to receive the bio sensor output signal, wherein the lock-in amplifier: amplifies the biosensor output signal, mixes the amplified biosensor output signal with the high-frequency drive signal, and frequency-filters the mixed, amplified biosensor output signal to output an impedance signal representing the low-frequency impedance variation resulting from the passage of the particle through the microfluidic channel.

In another aspect, this disclosure further provides a method for identifying or counting particles in a sample from a subject. The method comprises (i) obtaining from a subject a sample comprising particles, through a carrier configured to be attached to a subject; (ii) analyzing the sample by the impedance cytometer as described above; and (iii) determining a type or a count of the particles based on the outputted impedance signal representing the low-frequency impedance variation resulting from the passage of the particle through the microfluidic channel.

A. OVERVIEW

Increasingly capable smartphones and cheaper off-the-shelf components are constantly pushing what technology can achieve on-the-go. Robust and powerful electronics are driving progress for medical devices, which can be chronically worn or implanted. With current capabilities of digital technology, data sharing, and cloud processing, scientists envision a virtual medical system for providing continuous patient-centered care remotely. Being able to monitor body health is crucial for early detection of illness, which in turn would allow for more accurate diagnosis, more efficient treatment, and lower morbidity or health repercussions.

However, there are tight budget constraints and medical criteria, which biomedical devices must be approved for by the FDA to enter the market when considering wearability or implantability, such as weight and size, biocompatibility, aesthetic factors, and power consumption. Many procedures have been performed in labs for decades with expensive and bulky equipment, which have yet to be translated to wearable health-monitoring technology. Nevertheless, the market for wearable devices has been rapidly growing due to recent achievements in developing miniaturized sensors. For example, due to the development of incredibly robust and miniature accelerometers with microscale processing, devices such as the Fitbit™ have entered today's market for monitoring heart rate and user exercise activity. In addition, a variety of flexible electronics are currently being developed by researchers to monitor perspiration for glucose levels and other biomarkers. Flexible materials are suitable for wearable devices as they offer superior portability, durability, and robustness.

In the laboratory setting, microfluidic procedures are commonly employed to gather biomedical information for purposes where only a few tens or hundreds of nanoliters of the sample are to be analyzed. Flow cytometry is a specialized technology whereby cells, biomarkers, and particles may be quantified. Cell counting is one application of flow cytometry and can provide significant insight into a patient's health. For example, flow cytometry can provide a complete blood count (CBC) test, which can yield information about low or high red blood cell (RBC), white blood cell (WBC), or platelet levels amongst many other specific biomarker counts. However, there are limitations to how often blood counts can be obtained, especially because blood samples must be analyzed each time by a professional using expensive and bulky equipment primarily located in the laboratory setting. There is a need to achieve portable, user-friendly systems to perform automated blood counts so that patient health can be continuously monitored outside of the lab without the need for professional intervention.

Further, moving away from expensive data acquisition hardware has been a challenge because microfluidic impedance cytometry requires reading highly sensitive signals on the scale of nanovolts which fall below the noise level of the environment. Lock-in amplification (LIA) is a method which is used to isolate such small signals, by using phase-sensitive detection (PSD). A voltage at an elevated reference frequency is modulated with the impedance response of the system, and the signal response is demodulated by mixing with the original excitation voltage and applying a narrow band-pass filter around the reference frequency.

However, even with LIA, the resulting signal's baseline may drift over an extended period, reducing the amount of post-gain amplification, which can be applied to the signal, and demanding the use of powerful data acquisition instrumentation with high-resolution (>16 bit) analog-to-digital converters (ADCs). In addition, a novel analog LIA architecture, adding a baseline drift subtraction stage followed by a high-gain amplification stage, can allow a low-resolution (e.g., 10-bit, 8-bit, or fewer) ADC on a microcontroller unit (MCU) to sample the data (~1 kHz frequency). Although inexpensive MCUs with high-resolution ADC chips are on the market, more bits per sample poses new challenges regarding processing performance and data transmission speeds. Therefore, using a low-resolution ADC can be preferable. Accordingly, an embodiment flow cytometer may be inexpensive, have a small footprint, and may accurately detect impedance changes as small as 0.01%. A Bluetooth module may also be used to transmit data between the microcontroller and the smartphone, allowing a user to initiate data sampling and plot data results on the smartphone. An easy-to-use user interface may be developed, and a system using certain elements described herein may include discrete components and yet not be packaged in a user-friendly manner to promote convenient usage outside of a laboratory.

In particular, this disclosure provides a portable and fully integrated system including an LIA, a microfluidic polydimethylsiloxane (PDMS) biosensor, a microcontroller, and a Bluetooth module all compacted onto a flexible circuit board in the form of a low-profile wristband with communication to a live smartphone readout through an Android™ application. Blood samples can be obtained via pin-prick and inserted into an inlet of a microfluidic channel for blood cell counting, for example. A medical professional can access the data remotely after the data are exported from the smartphone. Alternatively, a machine-learning algorithm in the smartphone application can be used to alert the patient about the possibility of illness in various embodiments.

Additionally, different biomarker counts can be obtained by interchanging different microfluidic devices which isolate a specific cell type. For instance, if one wishes to use the platform to count eutrophil (a type of white blood cell) to monitor for neutropenia (low neutrophil count), a high-risk case for cancer patients undergoing chemotherapy, the standard microfluidic PDMS chip described herein for example cell counting can be replaced with a microfluidic device for neutrophil purification.

An immediate benefit of the embodiment cytometer being packaged as a wearable wristband is ultra-portability. A wearable quantifier for cells or other particles can be utilized in a wide variety of biomedical and environmental applications. As an example of important health applications, a catheter can be coupled to embodiment cytometers, and complete blood cell counts (CBCs) can be obtained from patients on demand. This is similar to how temperature, blood pressure, and pulse oximetry measurements currently can be readily obtained by non-cytometry devices. On-demand measurements can be especially useful in an acute setting for patients undergoing surgery or trauma care, where medical professionals need to make quick decisions based on CBC results. Currently, large amounts of blood must be collected from patients and sent to a lab for analysis for CBC counts. Instead of sending samples to a lab, embodiment cytometers allow health workers in hospitals or in the field to wear blood analyzer on their wrists or other locations and to move from patient to patient, performing rapid analysis.

Ultimately, a wearable embodiment cytometer for continuous personal health monitoring applications may be built if the pin-pricking mechanism is replaced with minimally invasive microneedle or catheter-based impedance sensor, which continuously samples venous blood without the necessity for long intravenous tubes driven by bulky flow pumps. In the context of environmental monitoring, a wearable impedance cytometer on the wristband can be utilized by inspectors and workers in the field, where different environments must be sampled for different particle counts, such as inorganic elements in mines, bacteria, or other contaminates in water samples, for example. In difficult conditions where dexterity is reduced (in rivers, cold temperatures, etc.), a wearable device can be especially beneficial for performing quick analysis on-site, as opposed to collecting and organizing samples and returning to the lab for analysis.

By modifying the impedance cytometer, so that protein or nucleic acid biomarker measurements can be obtained, embodiments may perform other applications involving continuous monitoring of protein biomarkers. For example, following a cardiopulmonary bypass procedure (CBP), it is critical to monitor for biomarkers indicating inflammatory response. A systemic inflammatory response during a CBP can result in dysfunction or failure of vital organs, including multi-organ failure, and even death. Monitoring for complement, neutrophil, and platelet activation help indicate the onset of the systemic inflammatory response. However, typical CPB procedures involve sampling periods up to 1 hour. Adoption of an embodiment wearable and fully integrated analyzer can enable continuous biomarker quantification and allow for medical professionals to make decisions based on real-time data. A novel microfluidic immunoassay may be used in an embodiment cytometer to collect and sample blood continuously. Accordingly, there is a wide array of medical and environmental applications to which embodiment wearable impedance cytometers may be utilized. Described hereinafter are core elements of various embodiments, namely a microfluidic bio sensor chip, analog front end and communication circuitry, and an example application for a mobile device for data analysis and display.

More generally, embodiments may include the elements described in connection with FIG. 1A. Further, a specific example embodiment that has been built and tested as a wearable wristband formed of a flexible PCB, wirelessly connected to a smartphone, is further described hereinafter in connection with FIGS. 2-9.

B. IMPEDANCE CYTOMETER

Described herein are impedance cytometers that may be miniature and use lock-in amplification (LIA), which is a method that is used to isolate such small signals, by using phase-sensitive detection (PSD). A voltage at an elevated reference frequency may be modulated with the impedance response of the system, and the signal response may be demodulated by mixing with the original excitation voltage and applying a narrow band-pass filter around the reference frequency. LIA, therefore, may eliminate the need for a heavy, bulky Faraday shield.

Embodiments may include a novel analog LIA architecture with a baseline drift subtraction stage followed by a high-gain amplification stage to allow a low-resolution (e.g., 10-bit, 8-bit, or fewer bits) ADC on a microcontroller unit (MCU) to sample the data (e.g., at ~1 kHz frequency). Although inexpensive MCUs with high-resolution ADC chips are on the market, a greater number of bits per sample poses new challenges regarding processing performance and data transmission speeds. Therefore, using a low-resolution ADC can be preferable. Resulting, embodiment impedance cytometers can be inexpensive, with a small footprint, and can accurately detect impedance changes as small as 0.01%.

Embodiments may include a Bluetooth module to transmit data between a microcontroller on the cytometer and a smartphone, allowing the user to initiate data sampling and plot data results on the smartphone. Other embodiments may transmit data over other wired or wireless connections. Components may all be compacted onto a flexible circuit board in the form of a low-profile wristband or other wearable platform. A live smartphone readout may be provided through a smartphone application, for example. Blood samples can be obtained via pin-prick and inserted into an inlet of the microfluidic channel for blood cell counting. A medical professional may access the data remotely after the data are exported from the smartphone. As an alternative, a machine learning algorithm in the smartphone application may be used to alert the wearer about the possibility of illness.

One embodiment that has been built and tested includes a wearable microfluidic impedance cytometer implemented on a flexible circuit wristband with an on-line smartphone readout for portable biomarker counting and analysis. The platform contains a standard polydimethylsiloxane (PDMS) microfluidic channel integrated on a wristband, and the circuitry on the wristband is composed of a custom analog lock-in amplification system, a microcontroller with an 8-bit analog-to-digital converter (ADC), and a Bluetooth module wirelessly paired with a smartphone. The lock-in amplification (LIA) system is implemented with a novel architecture that includes the lock-in amplifier followed by a high-pass filter stage with DC offset subtraction, and a post-subtraction high gain stage enabling detection of particles as small as 2.8 µm using the 8-bit ADC.

An Android™ smartphone application has been used in this built and tested embodiment to initiate the system and for offline data-plotting and peak counting. The application supports online data readout, analysis, and file management. The data is exportable to researchers and medical professionals for in-depth analysis and remote health monitoring. The system, including the microfluidic sensor, microcontroller, and Bluetooth module, all fit on the wristband with a footprint of less than 80 cm². Demonstrated herein is the ability of the system to obtain generalized blood cell counts. Nonetheless, the system can be applied to a wide variety of biomarkers by interchanging the standard microfluidic channel with microfluidic channels designed for biomarker isolation.

The particle may be from the living being, wherein the living being is a first living being, from the environment, or from a second living being. The particle can be a cell, a bacterium, a virus, a protein, a microparticle, a nanoparticle, a nucleic acid, a biomarker, or a bead with a biological material attached thereto. In some embodiments, the particle can be any microbial cellular organism (e.g., bacteria, archaea, fungi, protozoa, algae, and viruses).

The cell according to this embodiment may be collected from any kind of multicellular organisms. Specific examples of the cell include somatic cells collected from mammals (e.g., a human, a mouse, a monkey, a pig, a rat) and cells obtained by culturing cells isolated from each mammal or each mammalian cell line. Examples of the somatic cells include: keratinous epithelial cells (e.g., keratinocytes); mucosal epithelial cells (e.g., tongue epithelial cells); exocrine epithelial cells (e.g., mammary glandular cells); hormone-secreting cells (e.g., adrenomedullary cells); metabolic and storage cells (e.g., hepatocytes); interface-forming luminal epithelial cells (e.g., type I alveolar cells); vascular luminal epithelial cells (e.g., vascular endothelial cells); ciliated cells with transport function (e.g., tracheal epithelial cells); extracellular matrix secretory cells (e.g., fibroblasts); contractile cells (e.g., smooth muscle cells); hematopoietic and immune cells (e.g., T cells); sensory cells (e.g., rod cells); automatic nervous system neurons (e.g., cholinergic neurons); sensory and peripheral neuron-supporting cells (e.g., satellite cells); CNS neurons and glial cells (e.g., astrocytes); pigment cells (e.g., retinal pigment epithelial cells); and progenitors (tissue precursors) thereof. The cell differentiation degree and/or how old an animal, a source of the cell, is are not particularly limited. An undifferentiated progenitor (including a somatic stem cell) or a fully differentiated mature cell may be likewise used as a source of a somatic cell of the present invention. As used herein, examples of the undifferentiated progenitor include tissue stem cells (somatic stem cells) such as neural stem cells, hematopoietic stem cells, mesenchymal stem cells, and dental pulp stem cells. Preferable examples of an individual mammal which is a source of the somatic cell according to the present invention include, but are not particularly limited to, humans. In addition, more preferred are cells artificially processed after the somatic cells have been sampled. Examples include induced pluripotent stem cells (iPS cells) prepared from the somatic cells and cells obtained after pluripotent stem cells (e.g., ES cells and iPS cells) have been differentiated.

The microfluidic flow channel may be configured to receive the particle suspended in a bodily fluid (e.g., blood) or a buffer solution.

FIG. 1A is a block diagram illustrating an embodiment impedance cytometer 100. The impedance cytometer 100 includes a carrier 102 that is configured to be attached to a living being 104 using an attachment means 106. In various specific embodiments, the carrier 102 may be, for example, a rigid printed circuit board PCB, a complementary metal-oxide-semiconductor (CMOS) chip, or other rigid carrier that is capable of being attached to a living being.

Advantageously, as further described herein, in some embodiments the carrier 102 is a flexible printed circuit board. In general, the attachment means 106 may include a necklace, leg band, armband, wristband, or means such as loops or hooks on the carrier for attaching one of these types of bands to a human body. In some embodiments, including the flexible PCB armband described herein, the flexible PCB itself may provide the attachment means 106 by virtue of its shape to loop around an arm, wrist, leg, etc.

In FIG. 1A, the living being 104 is illustrated as having the impedance cytometer 100 connected to the waste by means of a belt 105. More generally, any type of waistband may be used that can secure the cytometer 100 to the living being 104 for use. In various embodiments, such as illustrated in FIG. 1A, the impedance cytometer need not be in contact with the skin of the living being, but instead may be worn outside clothing for convenient use. In other embodiments, however, the impedance cytometer may be attached and worn in close contact with the skin, either for convenience, or in order to receive bodily fluids, blood, or other samples from the living being 104. While the living being 104 illustrated in FIG. 1A is a human, embodiment impedance cytometers may be attached to other living beings, such as various animals, as will be understood in view of the disclosure herein.

As will be understood by those skilled in the art of microfluidic medical devices, a sample having a particle 112 to be analyzed may be received into the microfluidic channel (112) via an inlet of the microfluidic channel (not shown). For some embodiments, a sample may be obtained by a person living being wearing the impedance cytometer manually introducing a sample into the inlet of the microfluidic channel 112. In other example embodiments, a needle or an array of needles, such as those illustrated in FIG. 10, may automatically acquire a sample of blood or other material and introduce the sample into the inlet.

The impedance cytometer 100 includes a biosensor 108 mounted to the carrier 102. The bio sensor 108 includes a microfluidic flow channel 110 formed therein, and the channel 110 is structured and configured to accommodate passage of a particle 112 therethrough. In certain embodiments, the microfluidic flow channel 110 may be formed of polydimethylsiloxane (PDMS), for example. However, those of skill in the art of microfluidics will understand that other microfluidic flow channel materials may be used, depending on the nature of the particle and any buffer solution in which the particle 112 is suspended. In various embodiments, the particle may be a cell from the living being 104 or from another living being. Some embodiments may be configured to acquire particle samples from a patient, where the patient is the living being 104. However, the living being 104 may also be a clinician or other person, for example, who receives a particle 112 as part of a sample from other persons, animals, or even from the environment for sampling. Various embodiment cytometers within the scope of this disclosure may be configured to accommodate a cell, such as a blood cell, skin cell, or other cell, a bacterium, a virus, a protein, a microparticle, a nanoparticle, a nucleic acid, a biomarker, or a bead or other carrier particle with a biological material attached thereto.

The biosensor 108 further includes an impedance circuit 114. The impedance circuit 114 includes a signal generator 116, which is configured to produce a high-frequency drive signal 118. The drive signal 118 may be applied to the microfluidic flow channel 110 via electrodes, which are part of the impedance circuit 114 and are connected electrically to the flow channel 110, in that electrodes come into proximity with the channel and apply an electric field to the flow path within the channel. In various embodiments, such as in the embodiment illustrated in FIG. 2 and described hereinafter, the impedance circuit may also be mechanically attached to an inside or outside surface of the flow channel 110. The impedance circuit 114 may be configured, optionally, to have an electrical connection 120 to receive an output from an output electrode attached to the flow channel 110, for example, as described in connection with FIG. 2.

The impedance circuit 114 is configured to deliver a biosensor output signal 122. The biosensor output signal 122 has a high-frequency variation 124 that results from the high-frequency drive signal 118, as well as a low-frequency variation 126, which results from an impedance variation, within the microfluidic flow channel 110, during the passage of the particle 112 therethrough. The high-frequency variation 124 and low-frequency variation 126 of the biosensor output signal 122 are illustrated in the form of a graph in FIG. 1B. The example low-frequency variation 126, illustrated as a dashed line, could be obtained by taking a running time average of the biosensor output signal with the high-frequency component removed.

Figure 2:
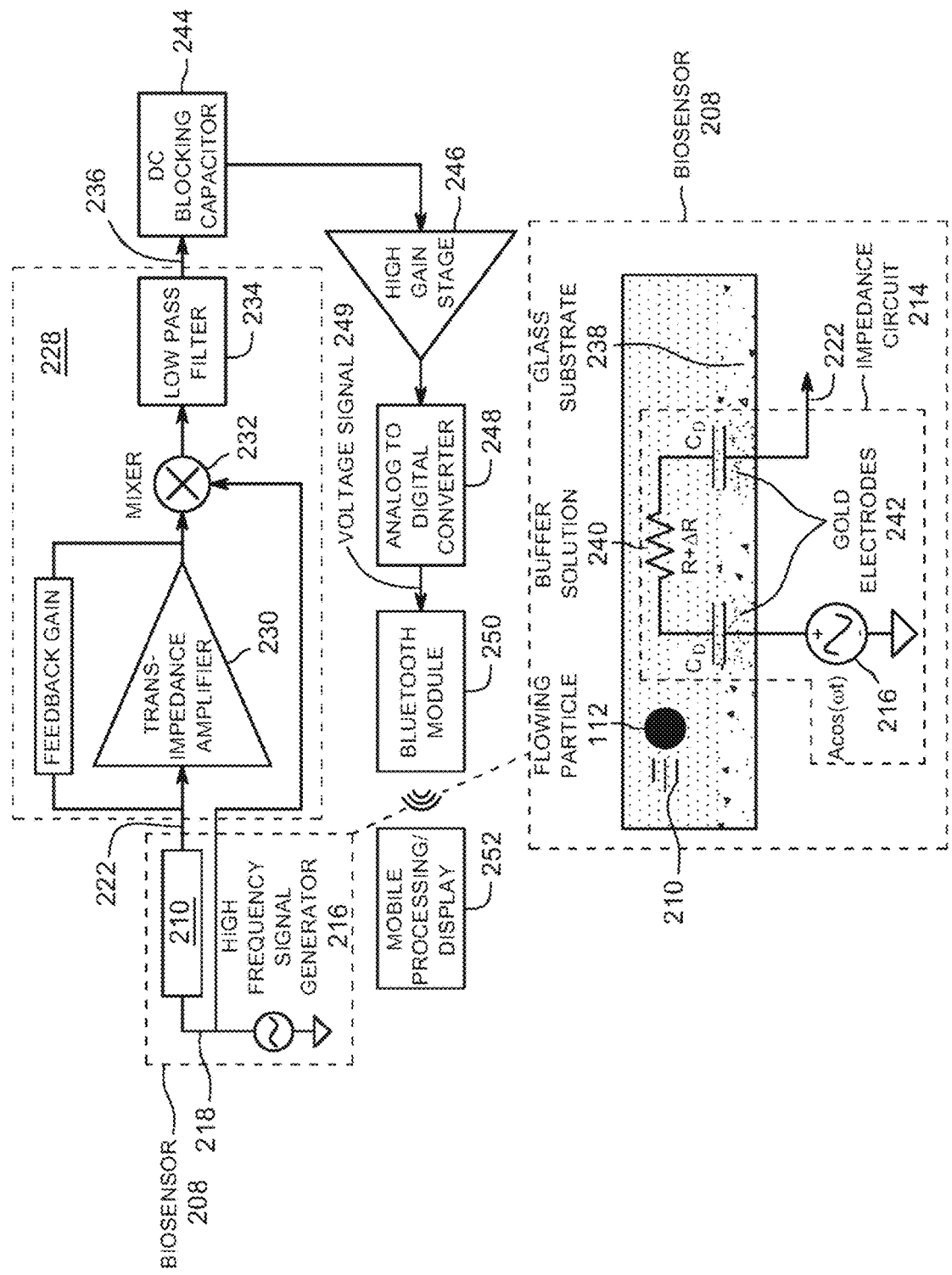
FIG. 2 is a schematic diagram illustrating biosensor and electrical details of an embodiment impedance cytometer, specifically a flexible wristband cytometer, which has been built and tested.

In FIG. 1A, the impedance circuit 114 is illustrated as a block separate from the flow channel 110 and having an electrical connection 120 as an output from the biosensor. The output from the electrical connection 120 may be the same as the biosensor output signal 122, as is the case in the embodiment described in connection with FIG. 2, for example. Furthermore, as illustrated in FIG. 2, the impedance circuit may encompass electrical components mechanically and electrically coupled to the microfluidic flow channel.

Figure 1C:
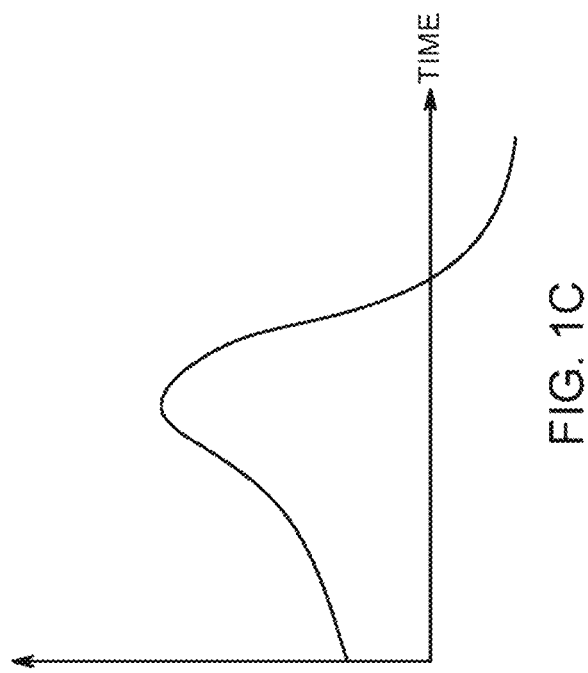
FIG. 1C is a graph illustrating an impedance signal output from a lock-in amplifier of an embodiment cytometer, the impedance signal comprising principally low-frequency variation.
Figure 1B:
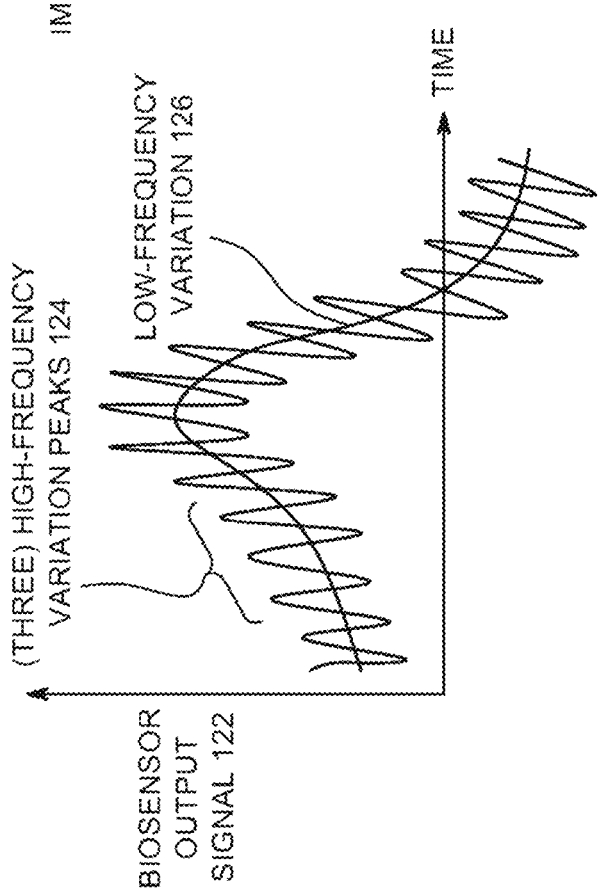
FIG. 1B is a graph illustrating a biosensor output signal output from an embodiment cytometer with high-frequency and low-frequency components.

The impedance cytometer 100 further includes a lock-in amplifier 128 that is configured to receive the biosensor output signal 122 and the high-frequency drive signal 118. The lock-in amplifier 128 includes an amplifier 130, which is configured to amplify the biosensor output signal. The lock-in amplifier 128 also includes a mixer 132, which is configured to mix the amplified biosensor output signal with the high-frequency drive signal 118. This mixing process may also be referred to as "multiplication," as will be understood by those skilled in the art of lock-in amplification. The lock-in amplifier 128 further includes a frequency filter 134, which is configured to frequency-filter the mixed, amplified, biosensor output signal to output an impedance signal 136. The impedance signal 136 represents the low-frequency impedance variation that results from the passage of the particle 112 through the microfluidic channel 110. FIG. 1C is a graph illustrating an example impedance signal 136, which may be similar to the low-frequency variation 126 that is present in the raw, biosensor output signal 122. The biosensor output signal 122 may also have other sources of high-frequency or low-frequency noise, from the environment, for example, which are not illustrated in FIG. 1B.

In some embodiments, the lock-in amplifier converts the current coming out of the electrode into a voltage using a transimpedance amplifier and then mixes the output voltage signal with a sinusoidal wave. Then the signal passes through a bandpass filter (or a low pass and then blocking capacitor), which eliminates high-frequency noise and also the baseline signal, and then through a high gain stage which amplifies the peaks. In the digital domain, a wavelet filter is used to reduce the noise. A threshold is set to cut off the noise and select the peaks.

In certain embodiments, various high frequencies may be used and analyzed for optimization of detection or characterization of various types of particles 112. Frequencies may be selected on the basis of particle size or other characteristics of the particle 112 that is sought to be analyzed. In cases involving multiple high frequencies, the high-frequency drive signal 118 may include different high frequencies at different times during passage of the particle 112 through the flow channel 110, or during passage of respective particles through the flow channel. The lock-in amplifier 128 may be configured to analyze different time portions of the bio sensor output signal 122 accordingly, using respective frequencies for the high-frequency drive signal 118 and appropriate, respective block and pass frequencies of the frequency filter 134 corresponding to different drive signal frequencies, for example. In some embodiments, frequencies for detecting cells range between about 100 kHz and about 20 MHz (e.g., 1 MHz).

Hereinafter, the specific example system architecture using a flexible PCB wristband and smartphone connection will be further described in depth, and then the construction of an accompanying flexible circuit board will be described, together with the fabrication of the biosensor and the mobile user interface for the system. To demonstrate the functionality of the overall platform, described hereinafter is its use to count polystyrene beads, sheep blood cells, and human blood cells as example particles. The analysis provided by the smartphone application working in connection with the embodiment wristband impedance cytometer described hereinafter is to detect and count individual particles.

a. System Architecture

FIG. 2 is a schematic diagram illustrating the custom-built analog architecture of the flexible wristband embodiment that has been built. The analog architecture is designed to detect highly sensitive impedance changes in a microfluidic channel with low-end hardware. A biosensor 208 includes a PDMS microfluidic flow channel 210 coupled to a high-frequency drive voltage signal 218 generated by a high-frequency signal generator 216. Gold electrodes 242 are present in a glass substrate 238 attached to the channel 210. The electrodes 242 couple the drive signal 218 to the channel and a bio sensor output signal 222 from the channel.

To perform traditional LIA using a lock-in amplifier 228, the voltage drive signal 218 at a high reference frequency is modulated with the microfluidic channel impedance, generating a biosensor output signal (in this embodiment, a current signal) 222. The biosensor 208 used in this work relies on an electric field generated between the two electrodes 242 within a microfluidic channel 210, with the baseline impedance R representing phosphate-buffered solution (PBS) 240, and variable impedance delta R resulting from the flow of the particle 112 through the electric field.

A transimpedance amplifier 230 then amplifies the input current signal 222 and outputs a voltage signal 236 ("impedance signal," as used herein), which is then mixed (using a mixer 232) with the original reference voltage signal 218. Finally, a low-pass filter 234 isolates the low-frequency component of the product, which is a low-noise signal proportional to the channel impedance amplitude at the reference frequency. As the channel impedance may also vary with time, this embodiment includes a low-pass filter cutoff frequency that is larger than the inverse of the transit time of the microfluidic particle, or the time it takes for the particle to transverse the field between electrodes as it flows through the channel.

After performing traditional LIA on the bio sensor output signal 222, there remains a DC offset within the filtered signal, which is in addition to the time-varying signal of interest. The DC offset limits the gain that can be applied to the signal before clipping occurs, and a novel use of a DC-blocking stage 244 (a DC blocking capacitor, in this embodiment) is used to subtract the offset and apply a post-subtraction high-gain amplification stage 246. The result is a highly sensitive architecture, which can be implemented with a small footprint and off-the-shelf components. For an in-depth analysis on the architecture, including noise analysis and simulation, further information is available in Talukder, N. et al., Biomed. Micro. 19, 36 (2017), which is hereby incorporated herein by reference in its entirety.

Significantly, the electrical sensitivity of the embodiments described herein can enable a Faraday cage to be eliminated. Various embodiments do not require a shell or box of metal to surround the impedance cytometer to get the needed sensitivity by blocking electromagnetic interference. Instead, the effects of any interference may be adequately eliminated using the electrical components described in connection with FIGS. 1A and 2, for example.

The DC blocking stage may cause a positive voltage peak to be followed by a negative voltage peak with the same integrated energy, giving the novel architecture a uniquely shaped peak signature, as illustrated hereinafter.

Because the analog signal has then been amplified over several orders of magnitude, a low-end ADC 248 in a microcontroller chip, for example, can sample the data. A digitized voltage output signal 249 (a digitized form of the impedance signal) is then output from the ADC 248. The microcontroller interfaces with a Bluetooth module 250 paired with a custom-developed smartphone application. The application can initiate data sampling, and for data processing, the readout and analysis illustrated in FIG. 2 in the form of a mobile processing/display block 252.

b. Flexible Circuit Configuration

Figure 3:
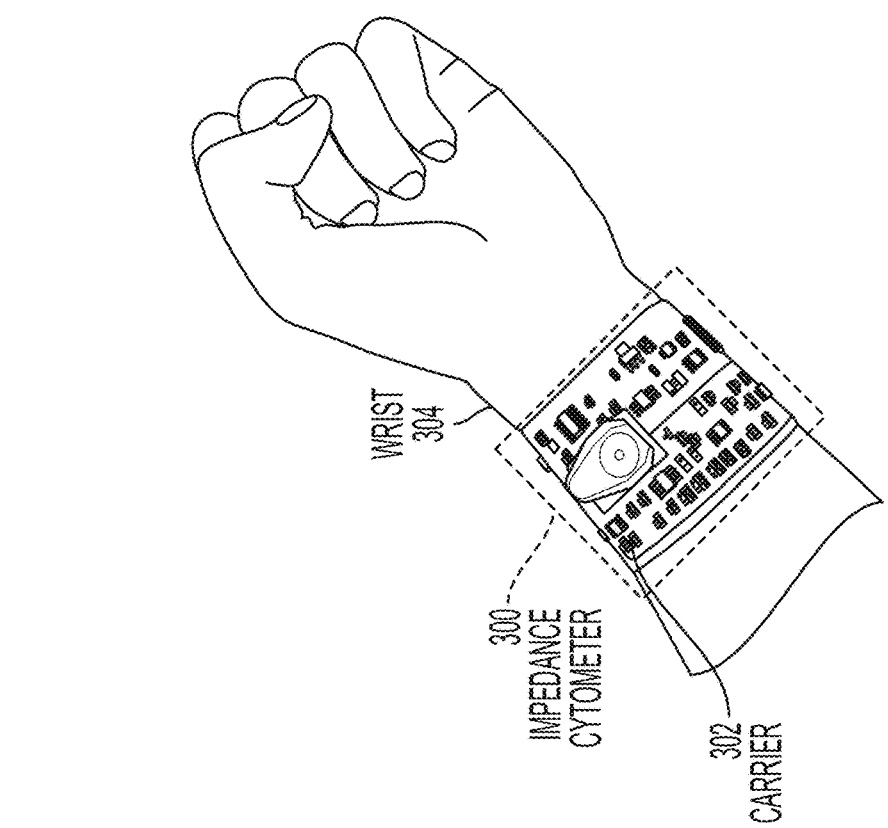
FIG. 3 is a photograph of the embodiment wristband cytometer, components of which are illustrated in FIG. 2, which has been built and tested.

FIG. 3 is a photograph showing a seamless and wearable microfluidic platform using a flexible circuit on a polyimide substrate carrier 302 in the form of a wristband to form a full embodiment wearable impedance cytometer 300. The carrier 302 shaped as a wristband is shown being worn on a wrist 304 of a living being (in FIG. 3, a person). The embodiment components of FIG. 2 have been implemented onto this carrier, except for the mobile processing/display 252. All components, such as batteries, a microcontroller, a Bluetooth module, and a biochip are unified onto one board. The flexible circuit is a two-layer polyimide board with copper traces totaling an area of 8 in$^2$. Surface-mount-packaged components were selected to compact the overall footprint and reduce noise.

It would typically be expected that impedance signals as small as those described herein would be overwhelmed even by noise from the conductance of the skin, preventing an impedance cytometer in contact with skin, such as the one illustrated in FIG. 3, from functioning. However, particular embodiment combinations of components have been described in connection with FIG. 1A, as well as the particular combination of electrical elements described in connection with FIG. 2, which forms part of the full embodiment wristband cytometer 300. Working together, these elements enable embodiment impedance cytometers to be effectively used in direct or close contact with a human body. This effectiveness is further described hereinafter in relation to data acquired using the wearable impedance cytometer 300.

Lightweight coin cell lithium-ion polymer (LIPO) batteries and regulator chips (LT1763 and LT1964 from Linear Technology) were used to provide ±5 V rails. A 1 MHz AC crystal oscillator (SG-210 from EPSON), D flipflop (74LS74D from Texas Instruments) for frequency division, and passive LC tank was used to generate the 500-kHz sine wave 2 Volt Peak-to-Peak (Vp-p) signal, which is excited through the biosensor. The glass wafer acting as the substrate for the biosensor was cut around the PDMS slab with a diamond scribe to minimize the dimensions and was attached to the board via microhook-tape and micro-loop-tape strips. The electrodes of the sensor interfaced with the board via jumping wires, which were first soldered to the circuit's terminals and then bonded to the sensor's terminals with conductive epoxy. Removal of the PDMS sensor involves de-soldering the jumping wires from the circuit board, separation of the microhook strip adhered to PDMS sensor from the underlying micro-loop strip adhered to the board, and vice versa for the addition of another sensor.

A DC-blocking capacitor was added prior to the biosensor to prevent low-frequency power surges from damaging the biosensor while the circuit was being switched on or off. The transimpedance stage following the bio sensor was implemented with a low-noise operational amplifier (TL071CP from Texas Instruments) and a potentiometer in the feedback path for adjustable gain from 0.04 to 0.44.

Mixing was achieved with a multiplier (AD835 from Analog Devices). To isolate the component of interest from the product of the mixing stage, a third-order Butterworth low-pass filter with a 100 Hz cutoff frequency and 60 dB roll-off per decade was designed with another TL071CP op-amp23. A DC-blocking capacitor was used for the DC-blocking stage. The last stage of the analog design, the high gain stage, was achieved with two more TL071CP amplifiers. The first stage has a gain of 1000, and the second stage uses a potentiometer to adjust the gain between 100 and 1100. The high gain stage was minimized during the experiment for a net gain of 105.

A Tiny 85 8-bit microcontroller from Atmel, driven by an external 16 MHz on-board crystal, was used to sample data. The microcontroller was programmed through the Arduino IDE (ARDUINO.CC) before being assembled on board. The HM-10 Bluetooth Low Energy (BLE) module was used for data transmission to the smartphone, with the module and the breakout circuit integrated on-board.

In addition to the wearable wristband, a wearable cytomter that fits into a pocket has also been reduced to practice. It wirelessly transmits the data to a mobile application.

c. Biosensor Fabrication

The process used to microfabricate the PDMS microfluidic channel for impedance cytometry is known. Channels with widths of 30 and 50 μm were used to obtain the example data described hereinafter, both 10-μm high and 1-cm long.

Figure 4:
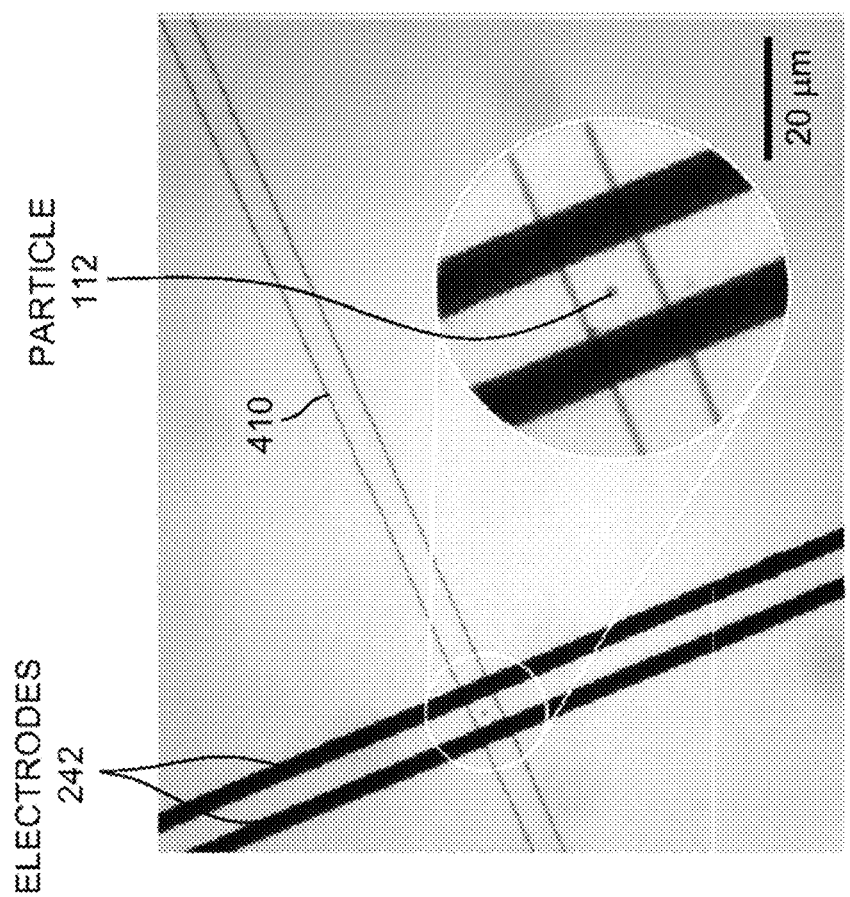
FIG. 4 is a top view photograph of a microfluidic PDMS flow channel pore with a sheep blood cell flowing therein, which was tested in connection with the embodiment of FIG. 3.

FIG. 4 is an aerial view of a 30 μm microfluidic flow channel 410 of the impedance cytometer 300. Also illustrated are gold electrodes 242 used to apply the electric field using the signal from the function generator 216. The electrode thicknesses selected were 500 nm Cr followed by 100 nm Au. For the 50 μm channel, the electrode finger design included 10-μm-wide fingers separated by 15 μm. For the 30 μm channel, the width of the fingers was 20 μm separated by 30 μm. The PDMS is intrinsically hydrophobic, preventing sufficient flow within the micro-channel. Poly (ethylene glycol)-based polymer containing dihydroxyphenylalanine and lysine (PEGDOPA-K) was used to improve hydrophilicity and lubricity of the PDMS, improving the flow of the particle 112.

d. Microfluidic Flow Channel

In some embodiments, the microfluidic flow channel is removably mounted in the biosensor. For example, the microfluidic flow channel can be configured as a plug and play cartridge suitable for receiving and analyzing different types of particles. In one example, the microfluidic flow channel can be configured for receiving red blood cells (RBCs), white blood cells (WBCs), hematocrit, hemoglobin, or a combination thereof. In another example, the microfluidic flow channel can be configured for receiving neutrophil, lymphocyte, or a combination thereof. In another example, the microfluidic flow channel can be configured for receiving microbial cells. In yet another example, the microfluidic flow channel can be configured for receiving and analyzing proteins present in blood or saliva, i.e., blood or saliva proteomics analysis.

In some embodiments, the present wearable cytometer includes a reader, which is the reusable unit that consists of the analog readout electronics, analog to digital converter, wireless transmission circuitry which transmits to a mobile device. Various cartridges can be plugged (plug and play) into the reader. The first type of cartridge performs a five-point complete blood count (CBC) measuring the red blood cell, white blood cell, and platelet concentrations along with hemoglobin and hematocrit levels. The second type of cartridge measures the total white blood cell count along with the differentials including neutrophils and lymphocytes. The third type of cartridge can be used for measuring microbial agents in the environment. Another cartridge measures protein concentrations in blood, saliva, and other bodily fluids.

One of the key challenges to the point-of-care blood analysis and wearable analysis of blood cells using impedance cytometry is the high concentration of red blood cells (millions of cells per microliter), which results in numerous cells crowding over the sensor. As a result, to obtain red blood cell count and hematocrit levels accurately, the sample needs to be diluted either off-chip or on-chip with a saline buffer. This process of dilution in itself results in variations in the concentration due to pipetting errors, making point-of-care analysis very difficult. For example, if only a prick of blood is obtained from the patient consisting of 10 microliters (with an error of +/−1 microliter), which must be diluted by 1000-fold before being analyzed by the cytometer. The result will be at least a 10% variation in concentration before a reading with the impedance cytometer is even performed. Thus, when dilution is required, the volume extracted must be very precise (within 1% error), which is hard to achieve.

Figure 11:
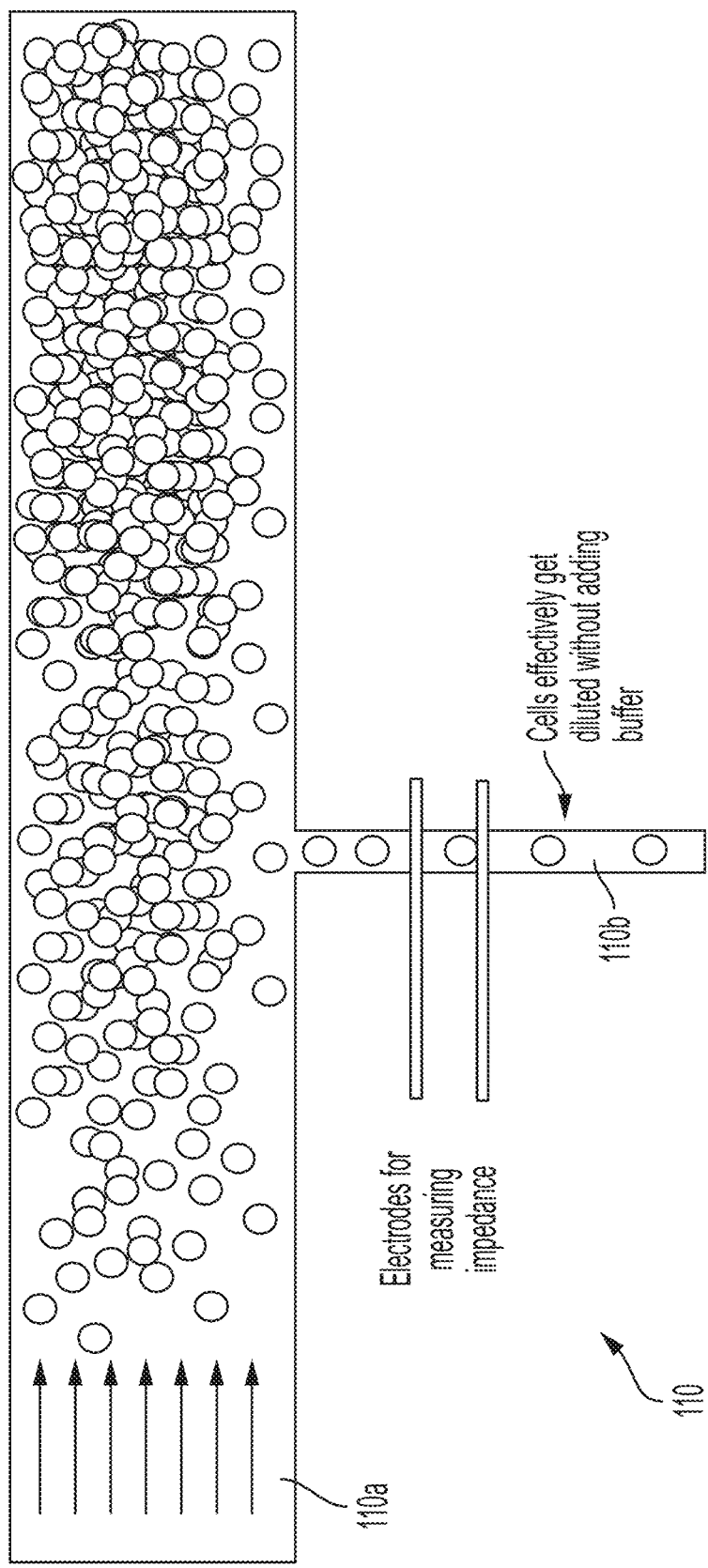
FIG. 11 shows an exemplary configuration of the microfluidic flow channel including a main channel and a side channel.

To address this issue, the present disclosure additionally provides a novel design of the microfluidic flow channel, which can avoid the need for dilution of the whole blood sample. Even if there are variations in the amount of blood collected from the user, the final results will be unaffected. In some embodiments, the microfluidic flow channel 110 may include a main channel 110a and a side channel 110b, as shown in FIG. 11. The side channel is attached to the main channel to divert a portion of the passage of the particle in the main channel.

The user may collect whole blood and place it into the inlet of the impedance cytometer chip to be analyzed. A wide channel can be used where the vast majority of the cells flow laterally from left to right. A narrow channel orthogonal to the main wide channel comes out the side. As a result of the Zweic-Fung effect, only a small fraction of the cells will be diverted into the side channel which leads to the impedance cytometer. In other words, rather than diluting the whole blood into a larger volume, we are using this physical mechanism to consistently divert a small fraction of the cells to the impedance cytometer. The Zwig-Fung effect is a natural mechanism discovered in nature in blood vessels and arteries. For the first time, to the best of the inventors' knowledge, this mechanism is used to solve the long-standing problem of RBC crowding in hematology analysis, which has either been handled by off-chip manual dilution or automated dilution inside analyzer through hydrodynamic focusing.

The main channel 110a may have the same or different dimensions relative to the side channel 110b. In some embodiments, the main channel has a larger width than the side channel. The side channel may be attached to the main channel in various fashions in order to divert the passage of particles in the main channel. For example, the side channel may be attached to the main channel in various orientations. In some embodiments, the side channel may be attached to the main channel in an acute angle, a right angle, or an obtuse angle. As shown in FIG. 11, the main channel 110a and the side channel 110b are orthogonal to each other.

In some embodiments, the particles in the side channel, diverted from the main channel, have a lower concentration than those in the main channel. For example, the concentration of the particles in the side channel can be between about 2 and about 5,000 folds (e.g., 5-fold, 10-fold, 20-fold, 30-fold, 50-fold, 100-fold, 200-fold, 300-fold, 400-fold, 500-fold, 600-fold, 700-fold, 800-fold, 900-fold, 1000-fold, 1200-fold, 1500-fold, 2000-fold, 2500-fold, 3000-fold, 3500-fold, 4000-fold, 4500-fold, 5000-fold) less than that of the particles in the main channel. Because particles in the side channel have a lower concentration than those in the main channel, they can be subject to analysis directly without the need for dilution. Thus, the side channel configuration of the microfluidic flow channel advantageously reduces the error generated during the dilution process and enables a streamlined process of analysis of particles.

e. Mobile Interface

Figure 5B:
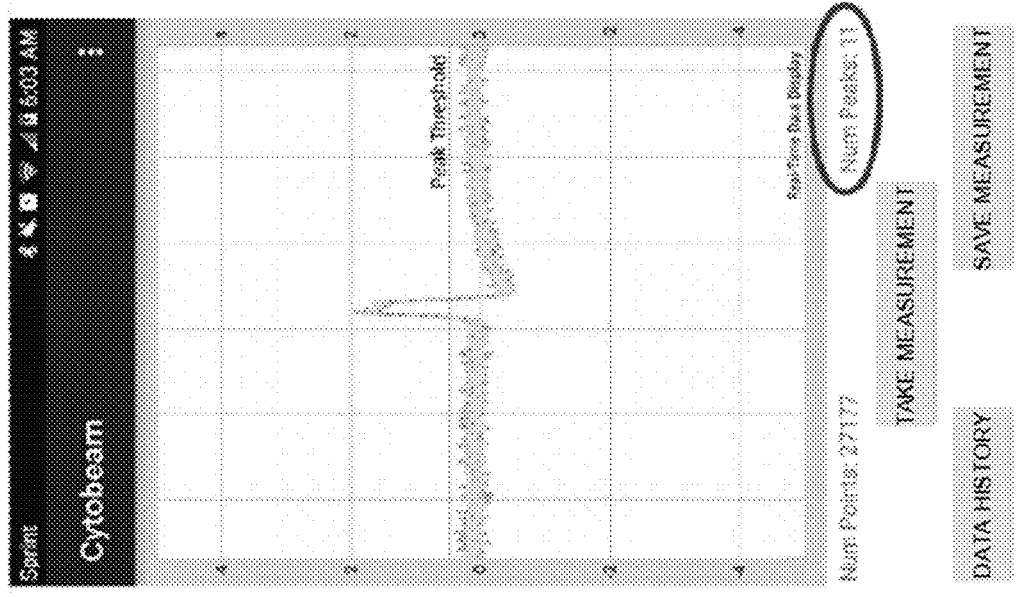
FIGS. 5A and 5B are a set of screenshots of a smartphone user interface used in connection with the embodiment wristband cytometer of FIG. 3.
Figure 5A:
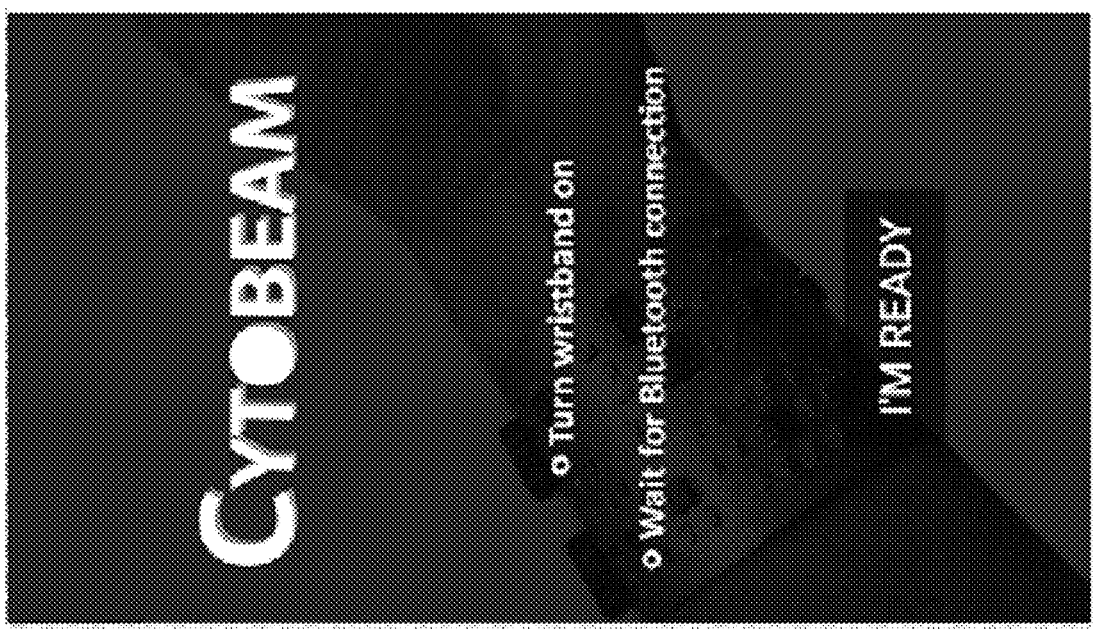
Figure 6A:
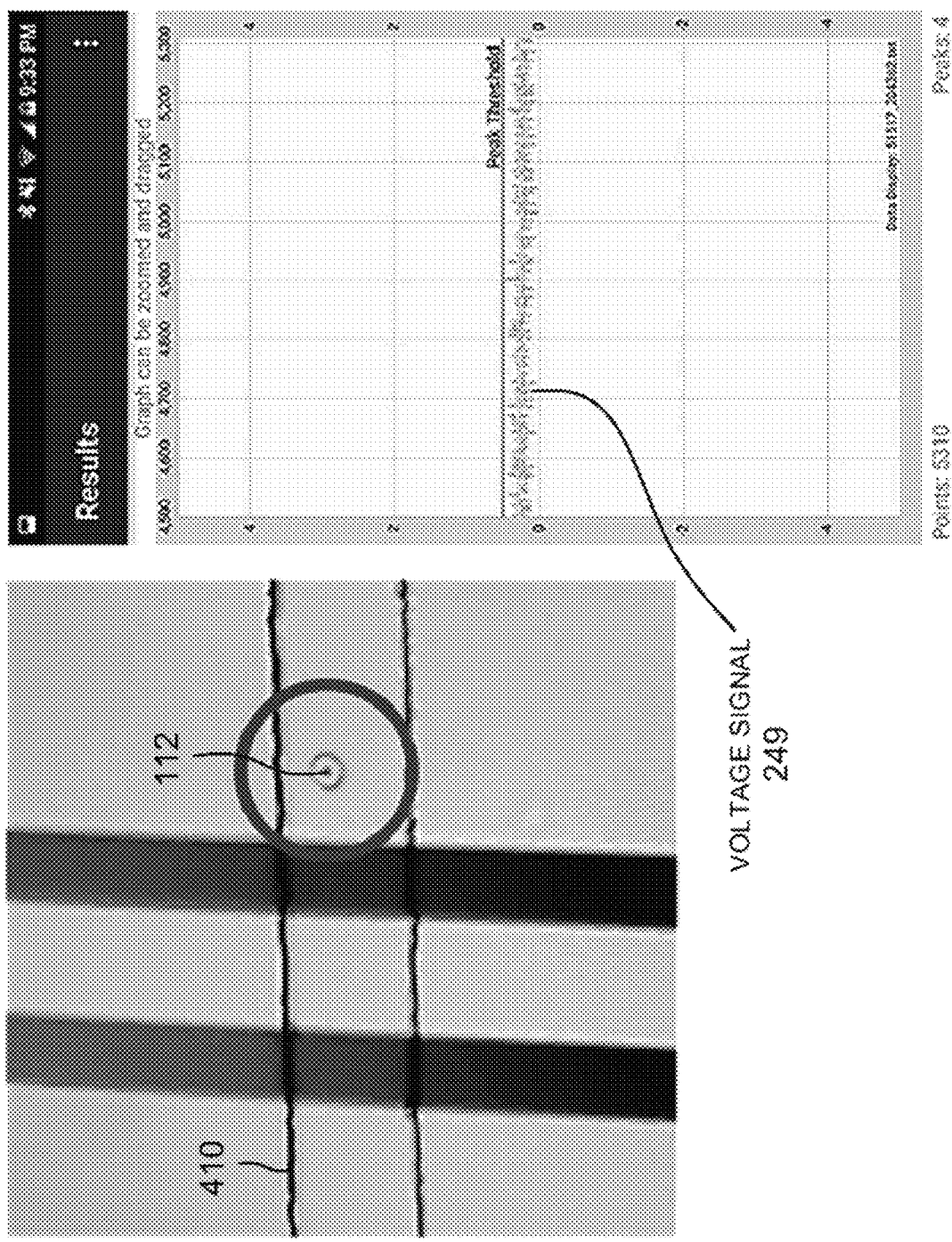
FIGS. 6A, 6B, 6C, and 6D are a set of screenshots from video and the smartphone interface of FIGS. 5A-5B recorded during a demonstration of the embodiment wristband cytometer of FIG. 3, with human red blood cells flowing, within a microfluidic flow channel, past electrodes situated therein.
Figure 6B:
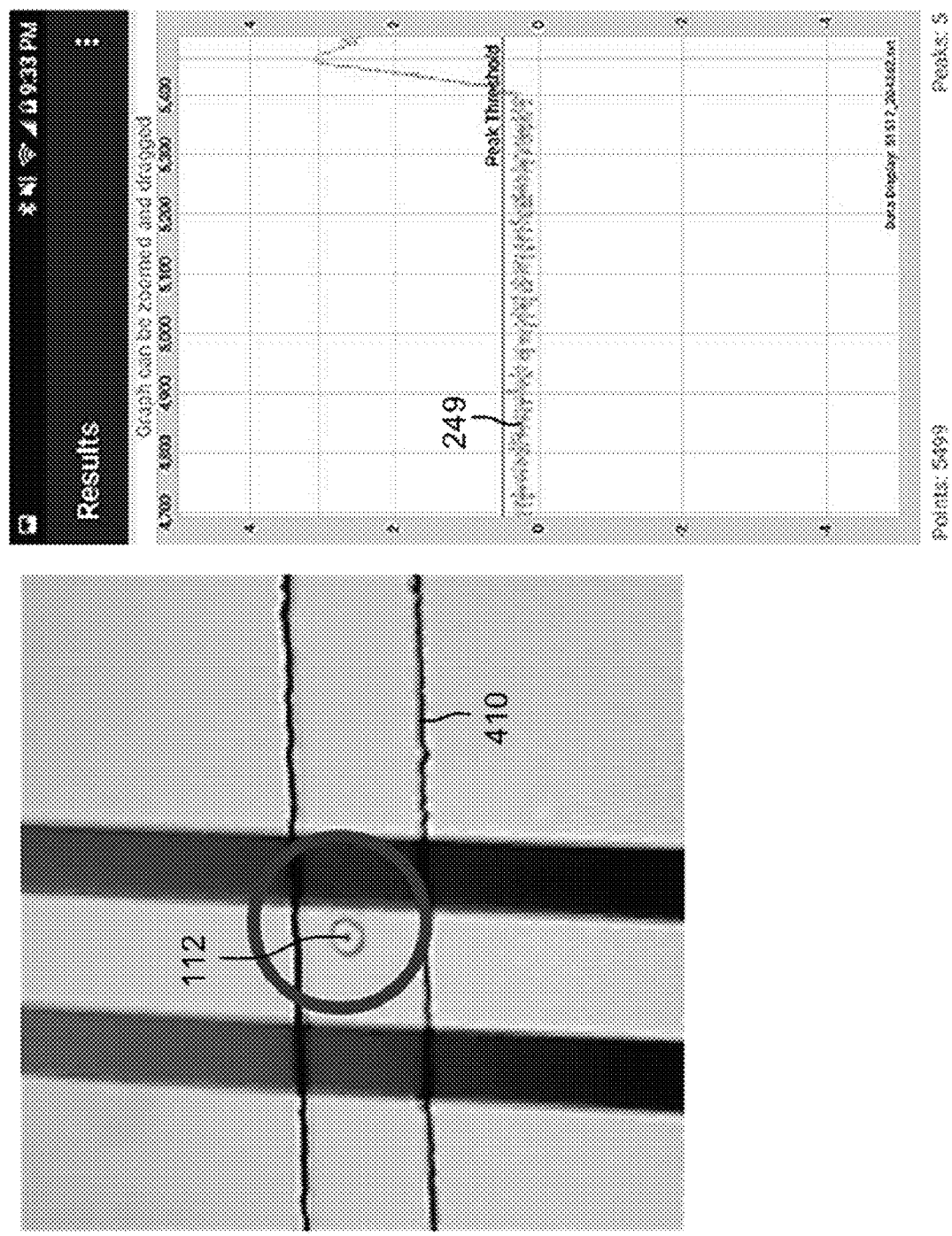
Figure 6C:
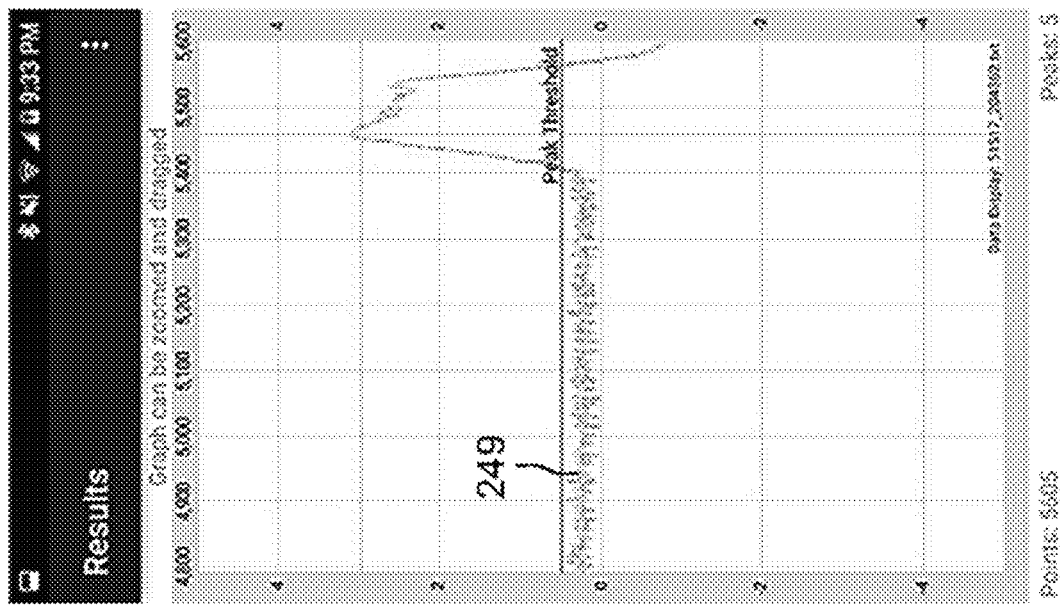
Figure 6C:
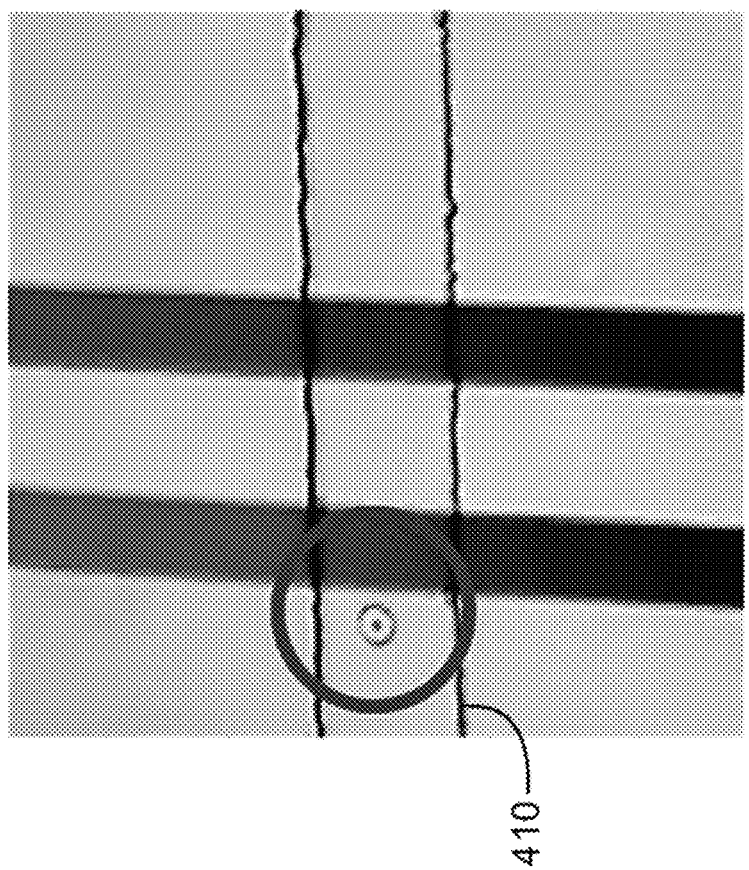
Figure 6D:
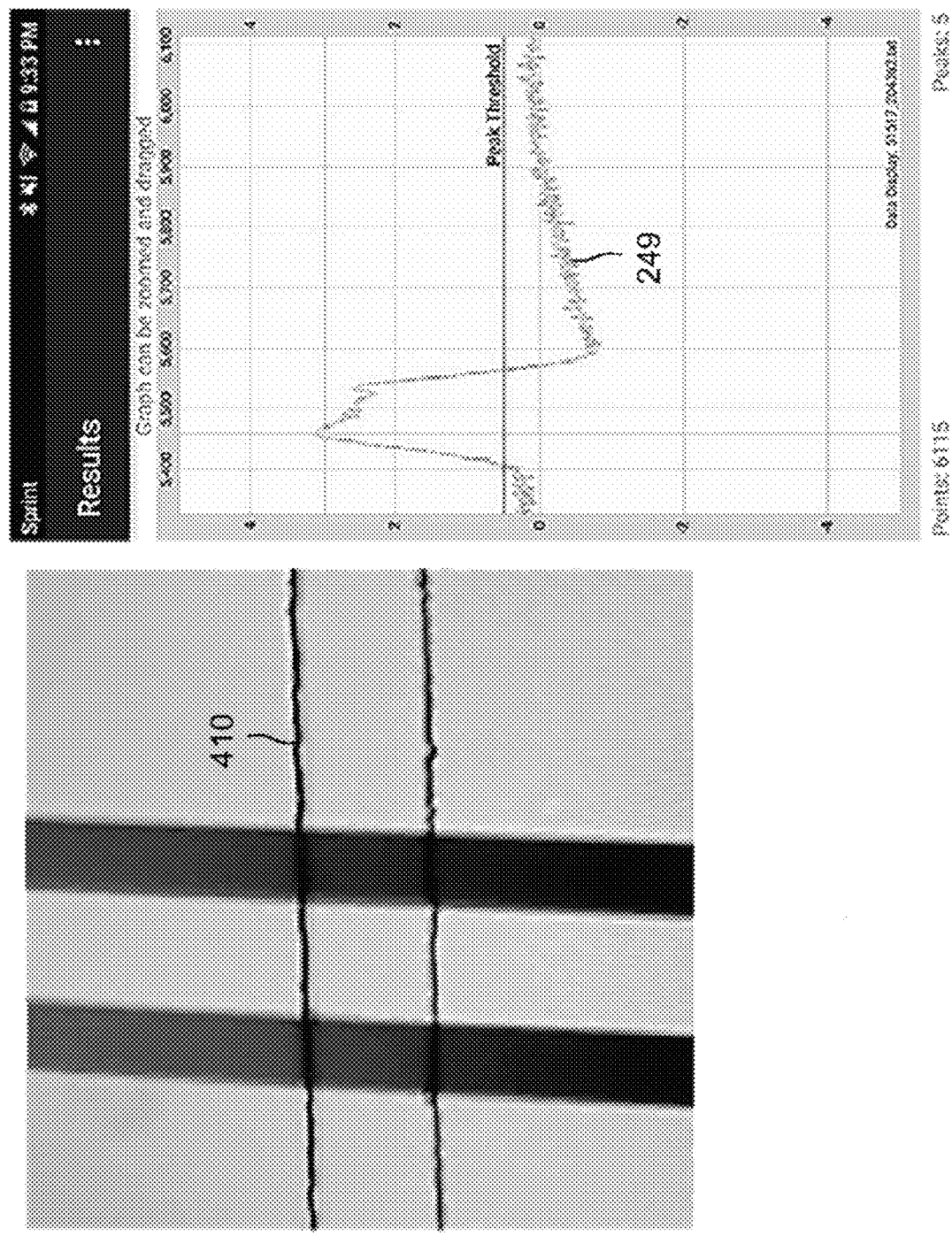

FIGS. 5A-5B are screenshots of a smartphone application developed to display results of the analysis of data from the flow cytometer 300. A Bluetooth Low Energy (BLE)-based application developed for this embodiment is designed to initiate data sampling from the analog circuit, save the data to storage, and plot the data post-sampling. The application features online data visualization and peak counting, as well as basic file management capabilities such as history data-plotting and data exporting. The application allows for the smartphone to serve as a replacement of the desktop software for the impedance spectrometer, optimized for the purposes of microfluidic particle counting. A specific advantage of online data readout that is used as part of this application is that during measurements, it the application has the ability to simultaneously record optical microscopic results on a computer screen and the electronic data results on a smartphone screen with a third-party video recording device, making post-experimental analysis and data alignment more efficient.

f. Data Analysis and Interpretation

After the data is sampled and converted to digital, the signal undergoes de-noising and also detrending (to remove any drift present in the solution). Multiple different signal processing algorithms have been tested here, including wavelets, band-pass filters, and also low-pass filters for denoising. For detrending, we have tested the use of median filters, high-pass filters, band-pass filters and also wavelet filters. The peaks are then identified using a thresholding function. If multiple peaks exist together, the two are decoupled from each other. Machine learning algorithms such as support vector machine, neural networks, have also been tested for classification of the peaks.

The peak data obtained can be analyzed in a fully automated manner using a combination of signal processing and also artificial intelligence. Both supervised and unsupervised learning classifiers can be used, however supervised learning is more straightforward. Different cell types such as platelets, RBCs, and WBCs can be classified based on impedance peak response. Even white blood cells can be differentiated from each other (e.g., lymphocytes, neutrophils, monocytes, etc.). Albeit more difficult, there is ultimately possibility of even classifying cells expressing certain antigens (e.g., CD4 positive and CD4 negative). The impedance cytometer would be trained by running pure samples of each cell type through the sensor. Features such as peak amplitude at different frequencies, peak area, half-width maximum, cepstral intensity, etc., can be used to improve accuracy. In addition to this machine learning can be used to correlate disease state to blood cell counts. For example based on the percentage of lymphocytes with respect to total white blood cell count or percentage of neutrophil with respect to total white blood cell count, infections can be classified as viral (increase in lymphocyte percentage) or bacterial (increase in neutrophil). Neutrophil and Lymphocyte cell population data (cell volume and conductivity) can also provide more specificity regarding if an infection is viral or bacterial. The smartphone application can also collect user data such as symptoms. The combination of the impedance cytometry data and the symptoms can be used as feature for training a machine learning classifier to accurately classify disease state.

C. EXAMPLES

Example 1

A minimalistic approach is used in the embodiment impedance cytometer 300 to circumvent traditional procedures requiring bulky and expensive equipment with new procedures that can be performed outside of the lab. As already described, the microfluidic PDMS channels used in the cytometer 300, including channel 410 in FIG. 4, were made hydrophilic by injecting a polyethylene glycol (PEG) solution using a micropipette into the well of the channel, as opposed to traditional oxygen plasma treatment. The use of PEG results in permanently keeping the channel hydrophilic. In contrast, when treated with oxygen plasma, the PDMS typically returns to its native hydrophobic state within tens of minutes. Because the device is sufficiently hydrophilic, no external pump is required to generate a steady particle flow. If isolation of a specific blood cell type was desired, instead of using centrifugation (the standard lab approach), passive microfluidic geometries for blood cell sorting, which are known, may be used, and these can be integrated into embodiment microfluidic platforms as needed.

The cytometer 300 was tested with blank PBS, PBS with 3 μm polystyrene beads, sheep blood cells, and human blood cells (<10% WBCs and platelets, >90% RBCs). All samples were diluted in 10 mM PBS with a dilution factor of 20 to reduce to the likelihood of clogging in our simple microfluidic channel, and the channels were filled with 10 mM, pH 7.4 PBS. A channel width of 50 μm was used when counting polystyrene beads and sheep blood cells, and a channel width of 30 μm was used when counting human blood cells obtained from finger pricks, corresponding to channel resistances of 12.5 kΩ and 20.8 kΩ, respectively.

To verify accuracy, an optical compound microscope was used alongside the digital readout system to verify the accuracy of the digitally reported particle counts. For the purposes of optical recording, the biosensor was removed from the surface of the board (while still connected to the system via jumper cables) and was positioned under the microscope so that the sensor's electrodes were visible under the field of view shown in FIG. 4. A digital camera was mounted onto the microscope lens so that the channel flow could be monitored on the desktop screen.

Simultaneously, the lock-in amplification system was turned on through a power switch. The Bluetooth module was paired with an Android smartphone running the custom Android™ smartphone application with the interface illustrated in FIGS. 5A-5B. Through the application, the microcontroller was prompted to begin sampling voltage data. The voltage data were then plotted in real-time on the smartphone application.

FIGS. 6A-6D show pairs of microscope view images (left of each figure) and voltage signals 249 shown on the smartphone application interface (right of each figure). As the data were being sampled, a third-party device was used to video record the microscopic view on a desktop computer screen and the voltage signal 249 on the smartphone.

FIGS. 7A-7D are graphs showing voltage signals 249, the results of 30 s experiments using blank PBS (no particle in the microfluidic flow channel), PBS with 3 μm polystyrene bead particles, sheep RBC particles, and human blood cell particles, respectively.

Figure 7E:
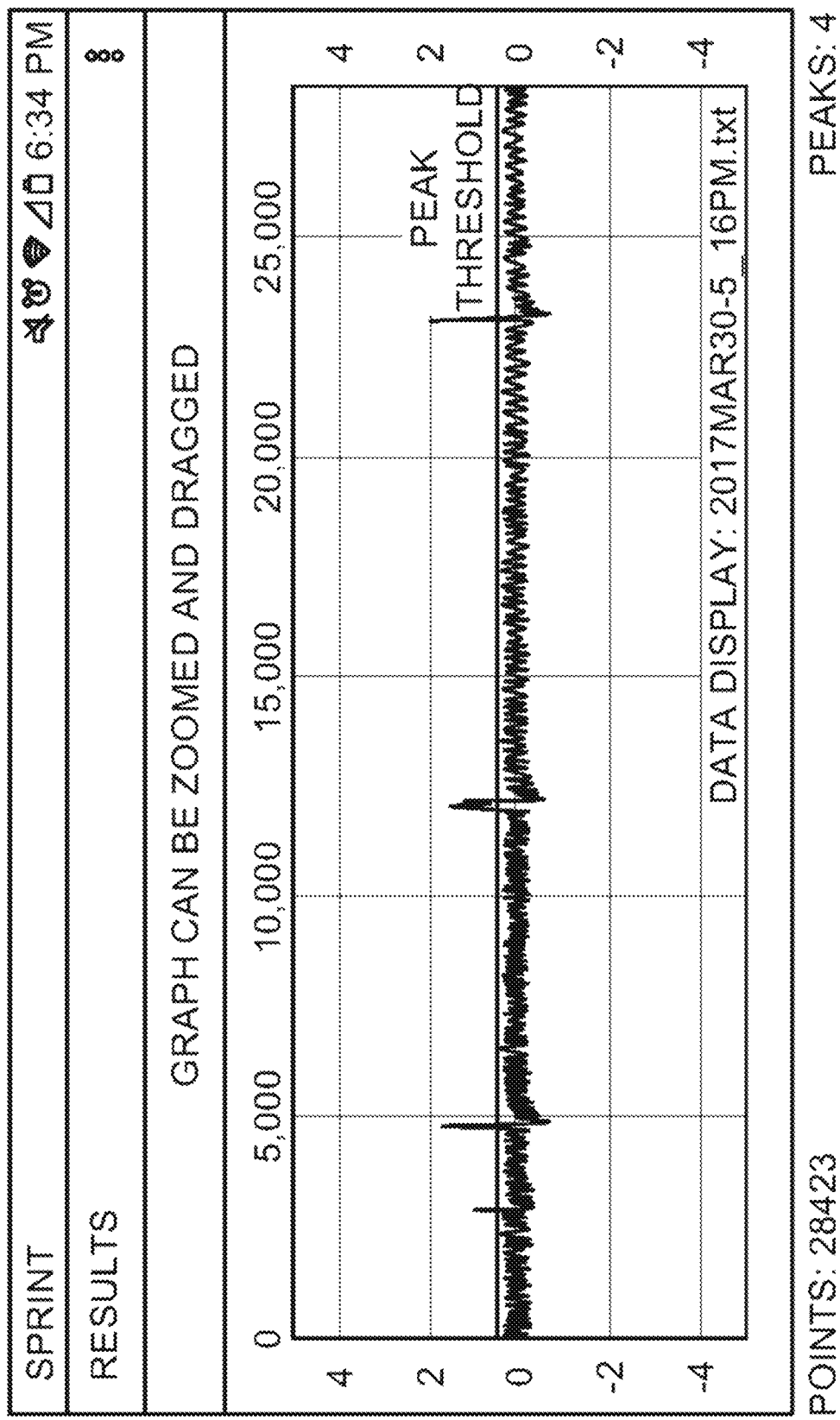

FIG. 7E shows the results of FIG. 7C, as displayed on the smartphone application interface. Due to the processing limitations of smartphone hardware, an efficient algorithm was targeted to count the number of particles flowing through the channel in live time. Therefore, a straightforward positive voltage threshold-based algorithm of 0.5 V was used to count the number of peaks in the smartphone. To remove false counts created by noise, a minimum quota was set, in which four consecutive samples of data were required to be above the threshold to iterate the peak count.

For longer experimental samples, with large amounts of data, post-experimental analysis were performed in MATLAB R2016a (MathWorks Inc.) for peak counting. An experiment was run with a duration of 10 min using human RBCs obtained via pin-prick and diluted in PBS in a 30-μm-wide channel. After the experiment, the data file was exported to a desktop computer. In some embodiments, a living being (patient) may similarly export his or her data remotely to a physician for detailed analysis. The data file can be opened in MATLAB, and a Butterworth band-pass filter has been applied using the Filter Designer from the MATLAB Signal Processing Toolbox. It can be helpful to filter out the DC component of the signal to remove drift, and to filter out high frequencies to create a smooth signal, without significantly affecting signal amplitude, as was done in some experiments described herein.

Figure 8A:
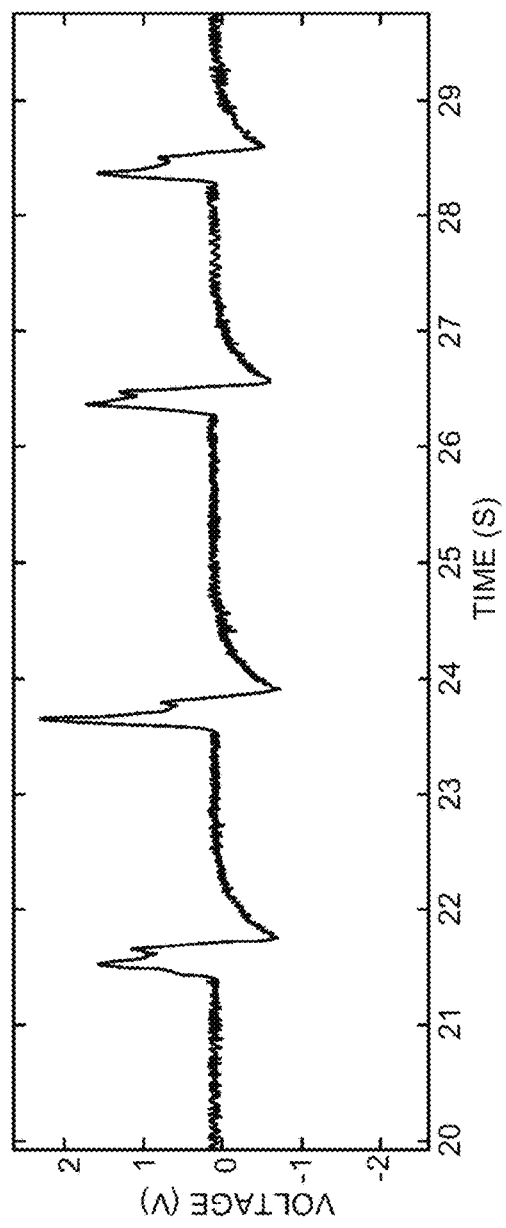
FIGS. 8A and 8B are graphs showing data from a 10-minute experiment with human blood cells in a 30-micron wide channel without modification and after applying a Butterworth band-pass filter, respectively.
Figure 8B:
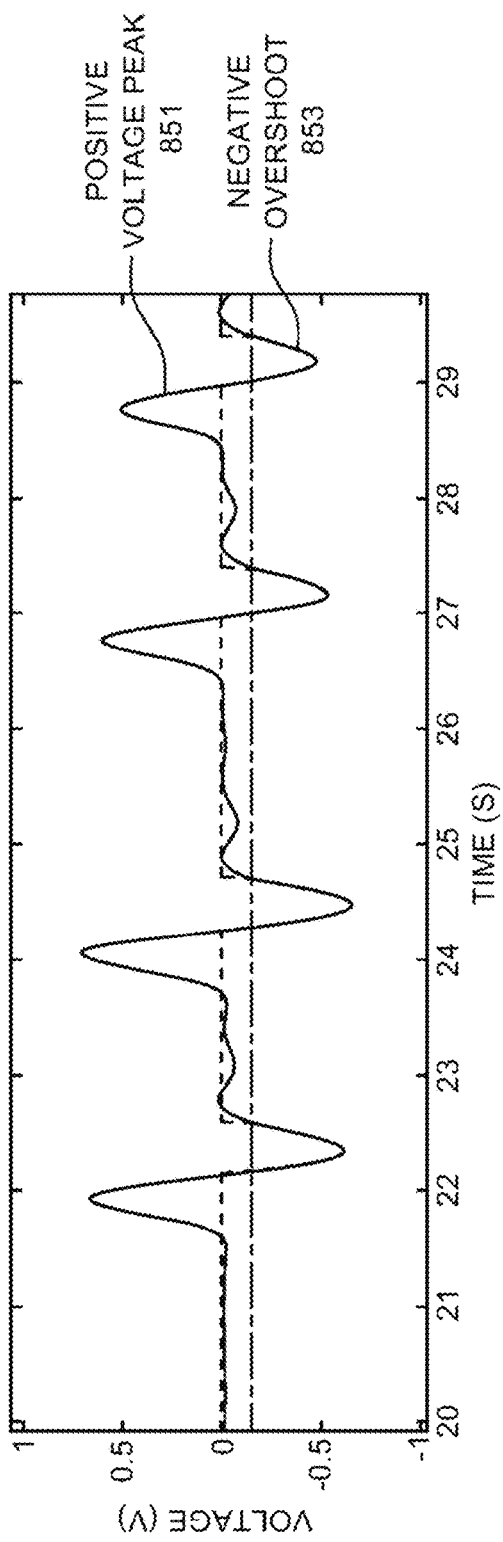

FIGS. 8A-8B show the resulting signals obtained using the post-experimental analysis process described above. In certain embodiment cytometers, a low-pass filter may be applied to the signal in live time. Negative voltage overshoot 853, caused by the DC-blocking capacitor 244, can help identify peaks with a higher accuracy than using an original positive voltage peak 851 in cases wherein cells or other particles flow through the electrodes in proximity to each other. Therefore, a negative threshold voltage can be applied to count the peaks in MATLAB, for example. The video recording of the experiment was compared to the MATLAB results to analyze optical count vs. digital count to determine accuracy of the cytometer 300 and related data analysis described herein.

Figure 9:
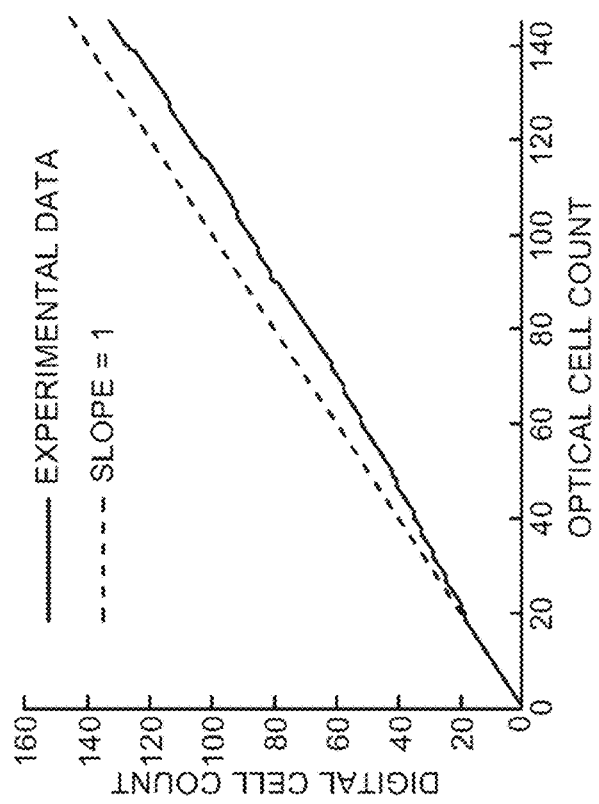
FIG. 9 is a graph showing a comparison of a cell count using the embodiment wristband cytometer of FIG. 3 and a cell count verified optically.

FIG. 9 is a graph showing a representative comparison of experimental data (solid line) with an expected result for perfect counting (dotted line).

When multiple cells (particles) flow between the electrodes at a given time, resulting in the overlap of separate voltage peaks, threshold-based automated counting, each occurrence of overlapping peaks can cause the digital-to-optical count ratio, as illustrated in FIG. 9, to drop. However, due to the unique peak signature from an embodiment circuit response, resulting from the DC-blocking capacitor 244, multiple known peak-fitting algorithms, such as those used in XPS analysis, can be implemented to obtain more accurate counts.

Figure 10:
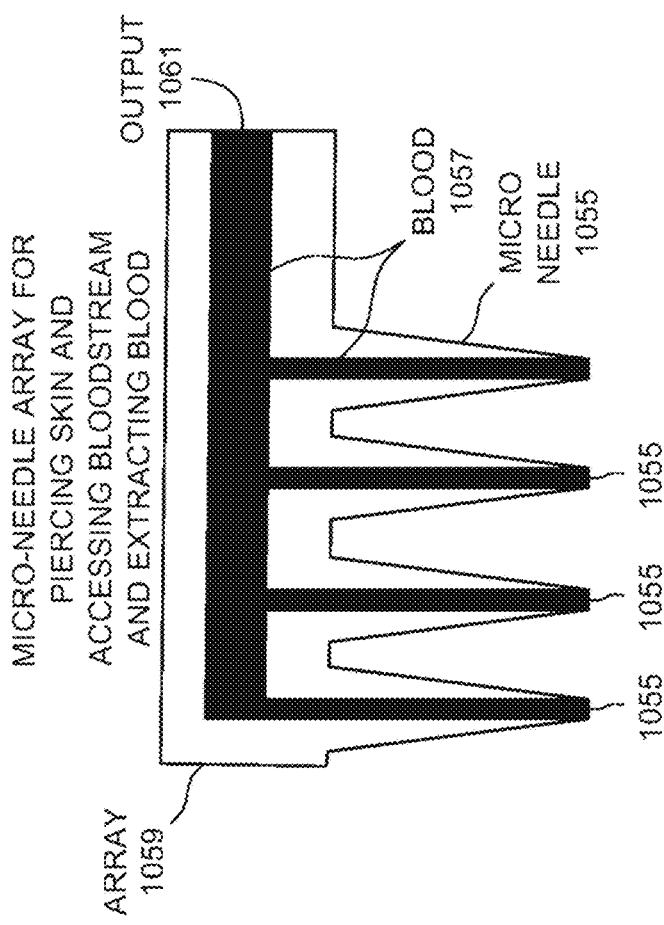
FIG. 10 is a diagram illustrating a needle array that may be used to obtain a blood sample in connection with embodiment impedance cytometers.

FIG. 10 is a diagram illustrating a micro-needle array 1059 that may be used to obtain a sample of blood 1057 in connection with embodiment impedance cytometers. In this example, the array 1059 includes four micro-needles 1055 to obtain the blood 1057. Though not shown in FIG. 10, the blood 1057 may flow from an output 1061 of the array 1059 to an input of a microfluidic flow channel used in embodiment cytometers.

Example 2

Figure 12:
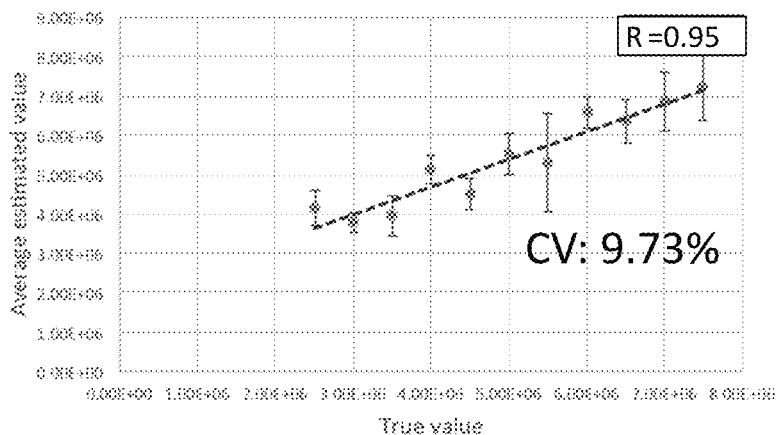
FIG. 12 shows an example application of the impedance cytometer for differentiating between platelets, red blood cells (RBCs), and white blood cells (WBCs).
Figure 12:
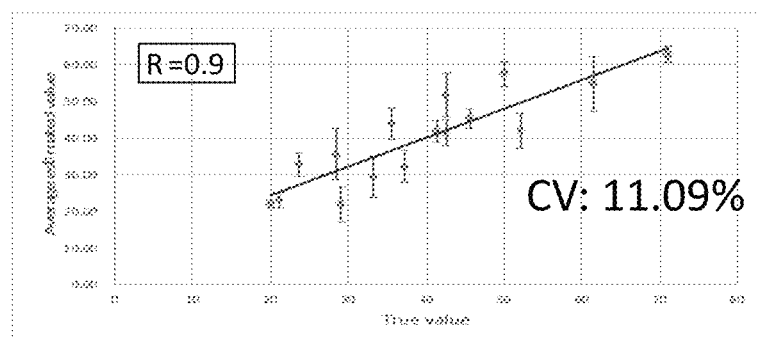
Figure 12:
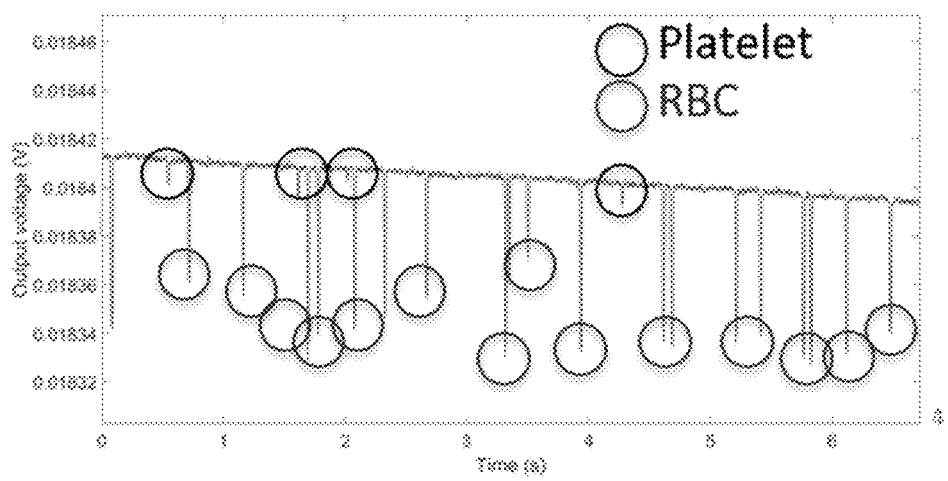

To differentiate between platelets, RBCs, and WBCs, the size (intensity of the peaks) was quantified, as shown in FIG. 12. Platelets are in the size range of 2-3 um, RBCs are in the size range of 6-8 um, and WBCs are greater than 10 um. Bottom plot of FIG. 12 shows peak signals due to platelets and RBCs. Small peaks circled in black are platelets and larger peaks circled in red are red blood cells.

Commercially available whole human blood samples were obtained and were characterized using a Beckman Coulter Hematology Analyzer to pre-characterize blood cell concentrations. The whole blood was diluted by 1000× and injected into the microfluidic impedance cytometer using capillary flow. The count was obtained, and concentration was calculated (count divided by volume). Fluid volume was calculated based on the amount of time that had passed and the flow rate of the cells (determined by peak transit time). The top curve shows the correlation curve between true count (obtained by Beckman Coulter) and the counts obtained by the wearable impedance cytometer. Hematocrit levels were obtained by measuring cell volume (proportional to peak intensity) and dividing by volume of fluid passed, which was calculated based on the amount of time that had passed and the flow rate of the cells (determined by peak transit time). In second plot, the comparison was made between hematocrit obtained with Beckman Coulter and the impedance cytometer.

Described herein is a wearable microfluidic impedance cytometer on a flexible substrate containing a microfluidic biosensor, analog readout hardware, and analog-to-digital data MCU, BLE transmission, operating together with smartphone data processing. Embodiments described herein can count the number of blood cells from a pin-prick blood sample pipetted into the standard microfluidic PDMS chip. Moreover, different types of biomarkers can be counted by replacing the standard PDMS chip with specialized microfluidic chips that isolate a specific biomarker. In the experimental embodiment described herein, interchanging the biosensors of the platform involves de-soldering and re-soldering jumping cables from the biosensor pads to the board. However, in other embodiments, this can be replaced with a more user-friendly plug and play packaging interface. The resulting voltage data can be exported and shared with a medical professional for in-depth analysis and can provide vital information to doctors without significantly disrupting a patient's daily schedule.

The circuit architecture, bio-sensor design, and overall packaging of embodiments may be modified to reduce the effects of motion and environmental disturbance and to test across a range of biosensors and biomarkers.

Multi-frequency impedance cytometry and data-driven approaches to discriminate between different cell types are also applicable to embodiments, using modifications that will be apparent to those skilled in the relevant arts in view of this disclosure. For the experimental embodiment described herein, the user can prick a finger and place samples into the microfluidic channel thus obtained, which must be performed at intervals and as opposed to continuous and automated blood counting. However, in other embodiments, a minimally invasive microneedle or catheter-based impedance sensor may be used to continuously sample venous blood using a wearable cytometry platform for readout. Bio-systems such as the embodiment impedance cytometers described herein, with some embodiments continuously monitoring human health, can be a key to early disease prediction and can revolutionize how medical professionals provide treatment to their patients.

D. DEFINITIONS

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

As used herein, the terms "subject," "patient," or "living being" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc) and a human). The subject may be a human or a non-human. In this context, a "normal," "control," or "reference" subject, patient or population is/are one(s) that exhibit(s) no detectable disease or disorder, respectively.

"Sample," "test sample," and "patient sample" may be used interchangeably herein. The sample can be a sample of, serum, urine plasma, amniotic fluid, cerebrospinal fluid, cells (e.g., antibody-producing cells) or tissue. Such a sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein purification may not be necessary.

Methods well known in the art for collecting, handling and processing urine, blood, serum, and plasma, and other body fluids, can be used in the practice of the present disclosure, for instance, when the antibodies provided herein are employed as immunodiagnostic reagents, and/or in an immunoassay kit. The test sample can comprise further moieties in addition to the analyte of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary, pretreatment optionally can be done for mere convenience (e.g., as part of a regimen on a commercial platform). The sample may be used directly as obtained from the subject or following a pretreatment to modify a characteristic of the sample. Pretreatment may include extraction, concentration, inactivation of interfering components, and/or the addition of reagents.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

As used herein, the term "diagnosis" means detecting a disease or disorder or determining the stage or degree of a disease or disorder. Usually, a diagnosis of a disease or disorder is based on the evaluation of one or more factors and/or symptoms that are indicative of the disease. That is, a diagnosis can be made based on the presence, absence or amount of a factor which is indicative of the presence or absence of the disease or condition. Each factor or symptom that is considered to be indicative of the diagnosis of a particular disease does not need to be exclusively related to the particular disease; i.e. there may be differential diagnoses that can be inferred from a diagnostic factor or symptom. Likewise, there may be instances where a factor or symptom that is indicative of a particular disease is present in an individual that does not have a particular disease. The diagnostic methods may be used independently or in combination with other diagnosing and/or staging methods known in the medical art for a particular disease or disorder.

The term "prognosis" as used herein refers to a prediction of the probable course and outcome of a clinical condition or disease. A prognosis is usually made by evaluating factors or symptoms of a disease that are indicative of a favorable or unfavorable course or outcome of the disease. The phrase "determining the prognosis" as used herein refers to the process by which the skilled artisan can predict the course or outcome of a condition in a patient. The term "prognosis" does not refer to the ability to predict the course or outcome of a condition with 100% accuracy instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition.

It is noted here that, as used in this specification and the appended claims, the singular forms "a," "an," and "the" include plural reference unless the context clearly dictates otherwise.

The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or sub-combination of the steps is encompassed within the scope of the disclosure, unless otherwise noted herein.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates, which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An impedance cytometer comprising:
   a carrier configured to be attached to a living being;
   a biosensor mounted to the carrier, the bio sensor comprising:
      a microfluidic flow channel formed therein, wherein the microfluidic flow channel is structured to accommodate passage of a particle therethrough; and
      an impedance circuit, connected to the microfluidic flow channel, wherein the impedance circuit includes a signal generator that produces a frequency drive signal that is applied to the microfluidic flow channel to produce thereby a biosensor output signal, and wherein the impedance circuit delivers a biosensor output signal having a high-frequency impedance variation which is a result from application of the frequency drive signal to the microfluidic flow channel, the biosensor output signal further having a low-frequency impedance variation which is a result from an impedance variation within the microfluidic flow channel during the passage of the particle therethrough; and
   a lock-in amplifier disposed to receive the biosensor output signal, wherein the lock-in amplifier:
      amplifies the biosensor output signal to produce an amplified biosensor output signal,
      mixes the amplified biosensor output signal with the frequency drive signal, and
      frequency-filters the mixed, amplified bio sensor output signal to output an impedance signal representing the low-frequency impedance variation resulting from the passage of the particle through the microfluidic channel.

2. The impedance cytometer of claim 1, wherein the microfluidic flow channel is removably mounted in the bio sensor.

3. The impedance cytometer of claim 1, wherein the microfluidic flow channel accommodates passage of a plurality of particles and wherein the microfluidic flow channel comprises a main channel and a side channel, the side channel being attached to the main channel to divert a portion of of the particles in the main channel.

4. The impedance cytometer of claim 3, wherein the main channel has a larger width than the side channel.

5. The impedance cytometer of claim 3, wherein the side channel is attached to the main channel vertically.

6. The impedance cytometer of claim 3, wherein a concentration of the particles in the side channel is about 2000 folds or less than a concentration of the particles in the main channel, thereby the particles in the side channel are subject to analysis without dilution.

7. The impedance cytometer of claim 1, wherein the carrier is further configured to be removably attached to the living being via any one of: a leg band, an armband, a wristband, a waistband, and a necklace.

8. The impedance cytometer of claim 1, wherein the carrier is a flexible printed circuit board (PCB).

9. The impedance cytometer of claim 1, wherein the lock-in amplifier comprises an amplifier, a mixer, and a frequency filter.

10. The impedance cytometer of claim 9, wherein the lock-in amplifier analyzes different time portions of the bio sensor output signal using respective frequencies for the frequency drive signal and corresponding respective block and pass frequencies for the frequency filter.

11. The impedance cytometer of claim 1, wherein the carrier is a complementary metal-oxide semiconductor (CMOS) chip.

12. The impedance cytometer of claim 1, wherein the microfluidic flow channel is formed of polydimethylsiloxane (PDMS).

13. The impedance cytometer of claim 1, wherein the particle is a cell.

14. The impedance cytometer of claim 1, wherein the particle is a bacterium, a virus, a protein, a microparticle, a nanoparticle, a nucleic acid, a biomarker, or a bead with a biological material attached thereto.

15. The impedance cytometer of claim 1, wherein the microfluidic flow channel is configured to receive the particle suspended in a bodily fluid or a buffer solution.

16. The impedance cytometer of claim 1, wherein the microfluidic flow channel is configured to receive the particle selected from the group consisting of red blood cell, white blood cell, platelet, hemoglobin, neutrophil, lymphocyte, microbe, and a combination thereof.

17. The impedance cytometer of claim 15, wherein the bodily fluid is blood.

18. The impedance cytometer of claim 1, wherein the signal generator is further configured to produce frequency drive signals with a plurality of frequencies.

19. The impedance cytometer of claim 18, wherein the plurality of frequencies comprises a frequency between about 100 kHz and about 20 MHz.

20. The impedance cytometer of claim 1, wherein the lock-in amplifier is further configured to frequency-filter the mixed, amplified bio sensor output signal with a low-pass filter cutoff frequency larger than an inverse of a transit time of the particle to traverse an electric field created by the frequency drive signal in the microfluidic flow channel.

21. The impedance cytometer of claim 1, further comprising a DC blocker configured to remove a DC baseline from the impedance signal and an amplifier configured to amplify an impedance signal with the DC baseline removed.

22. The impedance cytometer of claim 1, further comprising an analog-to-digital converter (ADC) configured to output a digitized form of an impedance signal.

23. The impedance cytometer of claim 22, wherein the ADC has 10 bits or fewer.

24. The impedance cytometer of claim 22, further including a wired or wireless transmission module configured to transmit the digitized form of an impedance signal.

25. An impedance cytometer system comprising the impedance cytometer of claim 24, further comprising: (a) a microprocessor configured to receive and analyze the digitized form of the impedance signal and (b) a display configured to show a result of an analysis of an impedance signal.

26. The impedance cytometer system of claim 25, wherein the result of the analysis includes a particle count, an identification of the particle, a characterization of the particle, or an indication of a health condition of the living being.

27. The impedance cytometer of claim 1, further comprising: (a) a microprocessor mounted to the carrier, the microprocessor configured to receive and analyze a digitized form of an impedance signal; and (b) a display mounted to the carrier and configured to show a result of an analysis of the impedance signal.

28. The impedance cytometer of claim 1, wherein the microfluidic flow channel is configured to receive the particle via a catheter, a needle, or an array of needles connected to the living being.

29. A method for identifying or counting particles in a sample from a subject, comprising:

obtaining from a subject a sample comprising particles, through a carrier configured to be attached to a subject;
analyzing the sample by the impedance cytometer of claim 1; and
determining a type or a count of the particles based on the outputted impedance signal representing the low-frequency impedance variation resulting from the passage of the particle through the microfluidic channel.

30. The method of claim 29, wherein the microfluidic flow channel is removably mounted in the biosensor.

31. The method of claim 29, wherein the microfluidic flow channel comprises a main channel and a side channel, the side channel being attached to the main channel to divert a portion of a passage of a plurality of particles in the main channel.

32. The method of claim 31, wherein the main channel has a larger width than the side channel.

33. The method of claim 29, wherein the carrier is further configured to be removably attached to the subject via any one of: a leg band, an armband, a wristband, a waistband, and a necklace.

34. The method of claim 29, wherein the lock-in amplifier analyzes different time portions of the biosensor output signal using respective frequencies for the frequency drive signal and corresponding respective block and pass frequencies for the lock-in amplifier.

35. The method of claim 29, wherein the lock-in amplifier is further configured to frequency-filter the mixed, amplified bio sensor output signal with a low-pass filter cutoff frequency larger than an inverse of a transit time of the particle to traverse an electric field created by the frequency drive signal in the microfluidic flow channel.

36. The method of claim 29, wherein the impedance cytometer further comprises a DC blocker configured to remove a DC baseline from an impedance signal and an amplifier configured to amplify an impedance signal with the DC baseline removed.

37. The method of claim 29, wherein the impedance cytometer further comprises an analog-to-digital converter (ADC) configured to output a digitized form of an impedance signal.

* * * * *